United States Patent
Stehr et al.

(10) Patent No.: US 12,305,165 B2
(45) Date of Patent: *May 20, 2025

(54) DEVICE FOR EXTRACTING A NUCLEIC ACID FROM A SAMPLE LIQUID

(71) Applicant: HP Health Solutions Germany GmbH, Gräfelfing (DE)

(72) Inventors: Joachim Stehr, Martinsried (DE); Lars Ullerich, Martinsried (DE); Federico Bürsgens, Martinsried (DE); Domenik Zistl, Martinsried (DE); Simon Schmidbauer, Martinsried (DE); Daniel Grodd, Martinsried (DE); Cecilia Rebuffo-Scheer, Martinsried (DE); Lidiya Osinkina, Martinsried (DE)

(73) Assignee: HP Health Solutions Germany GmbH, Gräfelfing (DE)

( * ) Notice: Subject to any disclaimer, the term of this patent is extended or adjusted under 35 U.S.C. 154(b) by 243 days.

This patent is subject to a terminal disclaimer.

(21) Appl. No.: 18/164,531

(22) Filed: Feb. 3, 2023

(65) Prior Publication Data

US 2023/0235314 A1 Jul. 27, 2023

Related U.S. Application Data

(60) Continuation of application No. 16/841,579, filed on Apr. 6, 2020, now Pat. No. 11,584,925, which is a
(Continued)

(30) Foreign Application Priority Data

Feb. 13, 2018 (DE) ...................... 10 2018 103 215.3

(51) Int. Cl.
*C12Q 1/68* (2018.01)
*B01L 7/00* (2006.01)
(Continued)

(52) U.S. Cl.
CPC ............ *C12N 15/1006* (2013.01); *B01L 7/52* (2013.01); *C12Q 1/6806* (2013.01); *C12Q 1/686* (2013.01);
(Continued)

(58) Field of Classification Search
CPC .............................. C12Q 1/6806; C12Q 1/686
See application file for complete search history.

(56) References Cited

U.S. PATENT DOCUMENTS 5,200,314 A   4/1993   Urdea
5,985,555 A   11/1999  Bertling
(Continued)

FOREIGN PATENT DOCUMENTS

EP   0415978 A1   3/1991
EP   1466018 A2   10/2004
(Continued)

OTHER PUBLICATIONS

DE102018103 215.3 English translation of allowable claims as of Nov. 27, 2018, pp. 4.
(Continued)

*Primary Examiner* — Kenneth R Horlick
(74) *Attorney, Agent, or Firm* — Foley & Lardner LLP

(57) ABSTRACT

A device for extracting a nucleic acid from a sample liquid includes a heating element configured to be connected to an extraction nucleic acid. The extraction nucleic acid is at least partly complementary to the nucleic acid to be extracted from the sample liquid. The heating element is heatable to a temperature that is equal to or higher than a denaturing temperature of the nucleic acid bound to the extraction nucleic acid.

20 Claims, 9 Drawing Sheets

Specification includes a Sequence Listing.

Related U.S. Application Data division of application No. 16/274,124, filed on Feb. 12, 2019, now Pat. No. 10,619,151.

(51) Int. Cl.
- *C12N 15/10* (2006.01)
- *C12P 19/34* (2006.01)
- *C12Q 1/6806* (2018.01)
- *C12Q 1/686* (2018.01)

(52) U.S. Cl.
CPC .................. *B01L 2200/0631* (2013.01); *B01L 2300/1827* (2013.01)

(56) References Cited

U.S. PATENT DOCUMENTS

| | | |
|---|---|---|
| 6,017,738 A | 1/2000 | Morris et al. |
| 6,090,592 A | 7/2000 | Adams et al. |
| 10,619,151 B2 | 4/2020 | Stehr et al. |
| 2002/0001811 A1 | 1/2002 | Collins et al. |
| 2002/0127569 A1 | 9/2002 | Weisburg et al. |
| 2017/0321278 A1 | 11/2017 | Germino et al. |

FOREIGN PATENT DOCUMENTS

| | | |
|---|---|---|
| EP | 1908849 A1 | 4/2008 |
| WO | 89/11546 A1 | 11/1989 |
| WO | 90/10716 A1 | 9/1990 |
| WO | 91/14788 A1 | 10/1991 |
| WO | 93/09250 A1 | 5/1993 |
| WO | 2013/113910 A1 | 8/2013 |
| WO | 2014/093934 A1 | 6/2014 |
| WO | 2015/006864 A1 | 1/2015 |
| WO | 2016/070945 A1 | 5/2016 |
| WO | 2017/127570 A1 | 7/2017 |

OTHER PUBLICATIONS

PCT/EP2019/052897 International Search Report and Written Opinion mailed Apr. 9, 2019, pp. 5.

Reddy B., et al., "Silicon Field Effect Transistors as Dual-Use Sensor-Heater Hybrids", Analytical Chemistry, vol. 83, No. 3, Feb. 1, 2011, pp. 888-895.

Renneberg, D., et al., "Watson-Crick base-pairing properties of Tricyclo-DNA", JACS Articles, May 7, 2002, vol. 124, pp. 5993-6002.

SEQUENCE LISTING

```
Sequence total quantity: 4
SEQ ID NO: 1           moltype = DNA  length = 23
FEATURE                Location/Qualifiers
misc_feature           1..23
                       note = Synthetic
source                 1..23
                       mol_type = other DNA
                       organism = synthetic construct
SEQUENCE: 1
tgaagatgtg cttacaagtg cta                                         23

SEQ ID NO: 2           moltype = DNA  length = 24
FEATURE                Location/Qualifiers
misc_feature           1..24
                       note = Synthetic
source                 1..24
                       mol_type = other DNA
                       organism = synthetic construct
SEQUENCE: 2
tccaccctca aacaggtgaa ttat                                        24

SEQ ID NO: 3           moltype = DNA  length = 35
```

```
FEATURE              Location/Qualifiers
misc_feature         1..35
                     note = Synthetic
source               1..35
                     mol_type = other DNA
                     organism = synthetic construct
SEQUENCE: 3
aaaaaaaaaa aaaaaaaaaa aaaaaaaaaa aaaaa                                35

SEQ ID NO: 4         moltype = DNA  length = 24
FEATURE              Location/Qualifiers
misc_feature         1..24
                     note = Synthetic
source               1..24
                     mol_type = other DNA
                     organism = synthetic construct
SEQUENCE: 4
aaatgattat ggctcaggta ctgc                                            24
```

DEVICE FOR EXTRACTING A NUCLEIC ACID FROM A SAMPLE LIQUID

CROSS-REFERENCE TO RELATED PATENT APPLICATIONS

This application is a continuation of U.S. patent application Ser. No. 16/841,579, filed Apr. 6, 2020, now U.S. Pat. No. 11,584,925, which is a divisional of U.S. patent application Ser. No. 16/274,124, filed Feb. 12, 2019, now U.S. Pat. No. 10,619,151, which claims priority to and the benefit of German Patent Application No. 102018103215.3, filed Feb. 13, 2018 in the German Patent and Trade Mark Office, the entireties of which are incorporated by reference herein.

SEQUENCE LISTING

The instant application contains a Sequence Listing which has been submitted electronically in XML format via Patent Center and is hereby incorporated by reference in its entirety. Said XML copy, created on Jan. 31, 2023, is named 86212710.xml and is 6,053 bytes in size.

TECHNICAL FIELD

The present invention relates to a method and to a device for extracting a nucleic acid from a sample liquid and optionally amplifying said nucleic acid. In particular, the invention relates to the field of extracting and/or purifying and/or amplifying nucleic acids, the amplification being carried out by means of a polymerase chain reaction (PCR) for example.

BACKGROUND

US2002/0127569A1 discloses a method for binding target polynucleotides in a sample by means of a solid support to which sample molecules are attached. Via capture probe molecules, the target polynucleotides can then be bound to the solid support together with the probe molecules. In this case, the solid support preferably consists of magnetic particles that can be removed from the solution by means of magnetic forces.

U.S. Pat. No. 6,090,592A discloses methods and devices for performing nucleic acid hybridization and amplification on a support. The hybridization conditions are preferably provided by a work station at which reagents or heating elements can be introduced, preferably through an opening.

WO91/14788 discloses methods and reagents for amplifying polynucleotides. In this case, the target sequence is purified and a PCR product detected. The target nucleic acid is bound to a solid support via other molecules. For the amplification, the solution is heated to a temperature between 90° C. and 100° C. for several minutes.

WO93/09250 discloses an assay and a method for amplifying and detecting target nucleic acids in patient samples. In this case, an amplification method is used in combination with primers that are immobilized on either a container or a dipstick.

Furthermore, EP1466018B1 discloses a method for purifying and amplifying a target nucleic acid, wherein the target nucleic acid is bound to magnetic glass particles.

EP0415978A1 discloses a method for analysing genes, wherein primers are bound to superparamagnetic particles. In this case, the temperature of the medium is altered by means of a metal block.

WO9010716A1 discloses a method for isolating and identifying a target nucleic acid in a sample, wherein the sample is bonded to a solid support to which a substrate is hybridized. The sample is heated by adding heated buffer solution.

The disadvantage of the methods known from the prior art is that extracting a nucleic acid to be copied is for the most part very complex and requires a considerable amount of time before the extracted nucleic acid can be amplified.

The object of the invention is therefore to provide a method and a device by means of which a nucleic acid can be extracted and optionally amplified in a short time and/or in a labour-saving manner.

SUMMARY OF THE INVENTION

The object is achieved by a method and a device having the features of the respective independent claims. The dependent claims and the following description relate to preferred embodiments.

In a first aspect, the invention relates to a method for extracting a nucleic acid from a sample liquid. The method comprises providing a heating element and providing an extraction nucleic acid that is bound to the heating element and/or providing the extraction nucleic acid such that the extraction nucleic acid binds to the heating element, wherein the extraction nucleic acid is at least partly complementary to the nucleic acid to be extracted from the sample liquid. The method further comprises bringing the heating element into contact with the sample liquid such that the nucleic acid to be extracted from the sample liquid at least partly binds to the extraction nucleic acid, and separating the heating element from the sample liquid such that the nucleic acid bound to the extraction nucleic acid remains at the heating element. Additionally, the method comprises bringing the heating element into contact with a reaction solution and heating the heating element to a temperature that is equal to or higher than a denaturing temperature of the nucleic acid bound to the extraction nucleic acid.

In a further aspect, the invention relates to a device for extracting a nucleic acid from a sample liquid. The device comprises a heating element, which is bonded or connected to an extraction nucleic acid and/or is designed so as to be bonded or connected to the extraction nucleic acid in this manner, wherein the extraction nucleic acid is at least partly complementary to the nucleic acid to be extracted from the sample liquid. In this case, the heating element is heatable, i.e. it can be heated, to a temperature that is equal to or greater than a denaturing temperature of the nucleic acid bound to the extraction nucleic acid in the prevailing surroundings, e.g. in the reaction solution. The denaturing temperature in the sample liquid may differ from the denaturing temperature in the reaction solution, wherein it is not strictly necessary for the heating element to be able to be heated to or above the denaturing temperature in the sample liquid.

In a further aspect, the invention relates to a use of a device according to the invention for extracting a nucleic acid from a sample liquid.

In the context of the present invention, the terms "nucleic acid" and "oligonucleotide" not only cover (deoxy)ribonucleic acids or (deoxy)oligo-ribonucleotides, even though these are preferred; they also cover nucleic acids and oligonucleotides that contain one or more nucleotide analogues having modifications on their backbone (e.g. methylphosphonate, phosphorothioate or peptide nucleic acids (PNA)), in particular on a sugar of the backbone (e.g. 2'-O-alkyl derivatives, 3'- and/or 5'-aminoriboses, locked nucleic acids (LNA), hexitol nucleic acids, morpholinos, glycol nucleic acid (GNA), threose nucleic acid (TNA) or tricyclo-DNA; see the essay "Watson-Crick base-pairing properties of Tricyclo-DNA" by D. Renneberg and C. J. Leumann, J. Am. Chem. Soc., 2002, Vol. 124, pages 5993-6002, the relevant content of which is part of this disclosure by way of reference), or contain base analogues, e.g. 7-deazapurine or universal bases such as nitroindole or modified natural bases such as N4-ethylcytosine. In one embodiment of the invention, the nucleic acids or oligonucleotides are conjugates or chimeras having non-nucleoside analogues, e.g. PNA. In one embodiment of the invention, the nucleic acids or oligonucleotides contain, at one or more positions, non-nucleoside and/or non-nucleotide units such as spacers, e.g. hexaethylene glycol or Cn-spacers where n is between 3 and 6. If the nucleic acids or oligonucleotides contain modifications, these are selected such that hybridization with natural DNA/RNA analytes is possible even with the modification. Preferred modifications influence the melting behaviour, preferably the melting point, in particular in order to be able to differentiate between hybrids having different degrees of complementarity in their bases (mismatch discrimination). Preferred modifications include LNA, 8-aza-7-deazapurine, 5-propynyl uracil and 5-propynyl cytosine and/or abasic breaks or modifications in the nucleic acid or oligonucleotide. Further modifications within the meaning of the invention are, for example, modifications using biotin and/or thiol and/or sulphur and/or fluorescence donor and fluorescence acceptor molecules.

The fact that the nucleic acid is extracted from the sample liquid means that the nucleic acid is at least partly isolated from the sample liquid and preferably can be separated from the sample liquid. The nucleic acid to be extracted from the sample liquid can also be referred to as the target nucleic acid. In particular, therefore, extracting a nucleic acid may comprise separating the nucleic acid from the sample liquid or serve for such a separation. In the process, the extraction of the nucleic acid may be designed such that only the nucleic acid to be extracted is extracted from the sample liquid, or such that other components of the sample liquid, such as other nucleic acids, are also extracted. Particularly preferably, however, only the nucleic acid to be extracted is extracted from the sample liquid, with the result that in particular other nucleic acids and other constituents of the sample liquid are not also extracted but instead remain in the sample liquid. Preferably, after extracting the nucleic acid, the concentration and/or the number of copies of the extracted nucleic acid in the sample liquid is lower than before the extraction, provided that the nucleic acid to be extracted was actually present in the sample liquid before the extraction. The fact that the extracted nucleic remains at the heating element preferably means that the extracted nucleic acid remains bound and/or connected and/or attached to the heating element.

In this case, the fact that the extraction nucleic acid is at least partly complementary to the target nucleic acid means that the extraction nucleic acid and the target nucleic acid can be hybridized together or bound to one another via at least one base pair. In other words, in its sequence, the extraction nucleic acid comprises at least one base that is complementary to at least one base of the target nucleic acid or the nucleic acid to be extracted. Preferably, however, the extraction nucleic acid has a higher degree of complementarity with the target nucleic acid; i.e. the base sequence of the extraction nucleic acid is preferably complementary to one or more portions of the target nucleic acid base sequence not only in one base, but rather in a plurality of preferably successive bases. More preferably at least 5, even more preferably at least 10, much more preferably at least 15, most preferably at least 20 base pairs, which are particularly preferably arranged successively without any other base pairs being arranged in between, are complementary to a corresponding sequence of the target nucleic acid. Preferably at least 1%, further preferably at least 5%, even further preferably at least 10%, more preferably at least 20%, even more preferably at least 30%, much more preferably at least 40%, even more preferably at least 50%, particularly preferably at least 60%, quite particularly preferably at least 70%, most preferably at least 80% and most preferably of all at least 90% of the extraction nucleic acid base sequence is complementary to a corresponding sequence of the target nucleic acid. According to a particularly preferred embodiment, the extraction nucleic acid can be substantially entirely complementary to a corresponding sequence of the target nucleic acid; i.e., apart from a few flaws, the extraction nucleic acid base sequence is entirely complementary to a corresponding sequence portion of the target nucleic acid. If the extraction nucleic acid comprises a plurality of different portions of base sequences, for example an extraction portion which is to serve for extracting the target nucleic acid and also a connection portion such as a spacer or a spacer sequence for spacing the extraction portion apart from the heating element, the above statements on the complementarity between the extraction nucleic acid and the target nucleic acid preferably relate solely to the extraction portion of the extraction nucleic acid.

A higher degree of complementarity between the extraction nucleic acid and the target nucleic acid may provide advantages in terms of the selectivity during the extraction. For instance, a high degree of complementarity between the extraction nucleic acid and the target nucleic acid may ensure that substantially only the target nucleic acid can bind to the extraction nucleic acid, whereas it would be exceptional for other nucleic acids from the sample liquid to bind to the extraction nucleic acid. On the other hand, a low degree of complementarity between the extraction nucleic acid and the target nucleic acid can preferably allow different nucleic acids from the sample liquid to bind to the extraction nucleic acid with the result that other nucleic acids from the sample liquid can also be extracted and/or the target nucleic acid can also be extracted when the extraction nucleic acid only has a low degree of complementarity therewith, for example because the base sequence of the target nucleic acid is not sufficiently known and, accordingly, the extraction nucleic acid cannot be precisely adapted to the target nucleic acid.

Preferably, at least one parameter of the sample liquid can be adapted to allow the target nucleic acid to hybridize to the extraction nucleic acid given the present degree of complementarity. For example, a concentration of $MgCl_2$ in the sample liquid can be increased to also enable hybridization in the case of low complementarity whilst, preferably, the concentration of $MgCl_2$ in the sample liquid can be lowered to enable hybridization only above a particular higher degree of complementarity.

The sample liquid is preferably a liquid that may comprise the nucleic acid to be extracted as well as other constituents. In particular, the sample liquid can comprise other constituents that are not intended to also be extracted. These other constituents may include other nucleic acids, i.e. nucleic acids having a different nucleotide sequence. The other constituents may also have impurities of a non-nucleotide nature. In particular, the sample liquid may be a liquid of, for example, human and/or animal and/or plant and/or other organic origin. For example, the sample liquid may contain or consist of blood and/or secretions and/or bodily excretions and/or mucosal discharges and/or saliva and/or cellular fluid. Preferably, the sample liquid can undergo one or more treatments prior to the extraction in order to at least partly release any nucleic acids contained in the sample liquid. For example, the sample liquid can undergo a treatment to lyse or break down any cells contained therein so as to at least partly release any nucleic acids contained therein from the cells, with the result that the nucleic acids are preferably present free in the sample liquid and, at least partly, are not or are no longer enclosed in cell nuclei and/or cells. The cells are preferably lysed such that the released nucleic acids are at least not entirely destroyed and particularly preferably are retained in full or remain intact.

In particular, the sample liquid can preferably be present such that it is not possible to perform an amplification reaction for copying the extracted nucleic acid in the sample liquid. For instance, the sample liquid can have physical and/or chemical and/or biological properties that prevent performance of an amplification reaction, such as, for example, a PCR, in the sample liquid. For example, the sample liquid can have a viscosity and/or a pH and/or a salt concentration and/or a polarity and/or enzymes and/or proteases that prevent the performance of an amplification reaction, for example because the activity of the polymerase enzymes required for this purpose is inhibited, or enzymes, such as proteases, are present that can degrade the polymerase enzymes.

The fact that the extraction nucleic acid is bound to the heating element means that the extraction nucleic acid is mechanically firmly bonded to the heating element, in particular by a chemical and/or electrostatic bond. For example, the extraction nucleic acid can be bound to a surface of the heating element by means of one or more thiol bonds and/or sulphur bonds. For this purpose, on at least part of its surface the heating element is preferably provided with a material that allows nucleic acids to bind. For example, a gold-plated surface can be used in order to bind the extraction nucleic acid, and optionally other nucleic acids, to the heating element via one or more thiol and/or sulphur bonds. A streptavidin-biotin bond can also be used, for example, to bind the extraction nucleic acid and/or other nucleic acids to the heating element, if for example one of the two partners (streptavidin or biotin) has been bound to the heating elements (preferably beforehand) and the extraction nucleic acid is modified (preferably at the 5' end) together with the other of the two partners and then bound thereby to the heating element. Other modifications such as, for example, amino or carboxy groups, can also be used to bind the extraction nucleic acid to the heating element; for this purpose, the surface of the heating element can be modified, preferably beforehand, using epoxy and/or a metal, for example. Preferably, a bond is established such that the 5' end of the extraction nucleic acid is bound to the heating element, with the result that the 3' end is free. This can be advantageous specifically when the extraction nucleic acid is intended to serve as a primer in an amplification reaction to be carried out following the extraction.

The fact that the extraction nucleic acid is provided such that the extraction nucleic acid binds to the heating element means that the extraction nucleic acid is brought into contact with the heating element under physical and/or chemical and/or biological conditions such that the extraction nucleic acid can bind to the heating element, in particular directly. For example, a temperature and/or a pH in a particular range may be required for this purpose. According to a preferred embodiment, the extraction nucleic acid is provided in the sample liquid such that the extraction nucleic acid binds to the heating element when the sample liquid is brought into contact with the heating element. In other words, the extraction nucleic acid is preferably provided in the sample liquid. For this purpose, the sample liquid particularly preferably has a physical and/or chemical and/or biological quality that allows the extraction nucleic acid to bind to the heating element. Preferably, the extraction nucleic acid is bonded to the heating element and/or can be bonded to the heating element such that the extraction nucleic acid bonded to the heating element is arranged in the reaction vessel or reaction solution.

The fact that the extraction nucleic acid binds and/or is bound to the heating element may mean that the extraction nucleic acid is directly or indirectly bound to the heating element. In the case of a direct bond, for example, one of the aforementioned binding types can bond the extraction nucleic acid directly to the heating element. In the case of an indirect bond, for example, the extraction nucleic acid can be bound to the heating element via an adapter nucleic acid, wherein the adapter nucleic acid is preferably firmly bound to the heating element, for example by means of a thiol bond and/or another of the aforementioned binding types, whilst the extraction nucleic acid can in turn bind to the adapter nucleic acid. Preferably, the extraction nucleic acid can hybridize with the adapter nucleic acid and indirectly bind to the heating element in this manner. This may provide the advantage that the heating element can be provided with one or more adapter nucleic acids and can be customized or adapted to the respective requirements in a simple manner by adding one or more extraction nucleic acids which are designed to bind to the adapter nucleic acid. Several extraction nucleic acids can preferably be bound to each heating element, wherein all the extraction nucleic acids are bound to the heating element either directly or indirectly via at least one adapter nucleic acid in each case. Alternatively, at least one extraction nucleic acid can preferably also be directly bound to a heating element and at least one extraction nucleic acid is or can be bound indirectly via an adapter nucleic acid.

The fact that the heating element is brought into contact with the sample liquid such that the nucleic acid to be extracted from the sample liquid binds at least partly to the extraction nucleic acid may mean that hybridization conditions that promote and/or enable hybridization of the nucleic acid being extracted with the extraction nucleic acid, at least partly prevail, at least on the contact surface between the heating element and the sample liquid, i.e. on the surface of the heating element and/or in the immediate surroundings. For example, the hybridization conditions may comprise a temperature and/or a pH and/or a salt concentration in a particular range. According to a preferred embodiment, the heating element can be heated in order to at least temporarily provide, in the immediate surroundings, the temperature required in order to enable the nucleic acid being extracted to hybridize with the extraction nucleic acid. According to another preferred embodiment, the heating element and the sample liquid can preferably also be heated as homogeneously as possible, i.e. such that the heating elements are at the same or approximately the same temperature as the reaction solution in order to allow the nucleic acid being extracted to effectively hybridize to the extraction nucleic acid. Preferably, this can be realized by the heating element and/or by an optional additional heating device preferably arranged outside the sample liquid.

For this purpose, the entire device containing the heating elements and the sample liquid can be heated to a base temperature of, for example, between 35° C. and 80° C. and particularly preferably between 40° C. and 70° C. Preferably, a base temperature of this kind can be set at least temporarily during the extraction. Optionally, during an optional amplification following the extraction, it is possible to forego setting the same base temperature and/or and to set a different base temperature or overall temperature of the reaction solution.

In this case, the denaturing temperature corresponds to a temperature at which a nucleic acid double strand is denatured, i.e. at which the nucleic acid double strand is separated into its two individual strands. For instance, in the denaturing step the extraction nucleic acid can be separated from the nucleic acid hybridized thereto. The type of denaturing preferred according to the invention is thermal denaturing (also referred to as "fusion"). For this purpose, at least a part of the nucleic acid double strand or the entire double strand is exposed to a temperature that is equal to or higher than the denaturing temperature that causes or at least promotes separation of the nucleic acid double strand. On the one hand, the preferred denaturing temperature is selected to be so high that nucleic acid double strands can be split. On the other hand, the preferred denaturing temperature is selected to be so low that a DNA polymerase potentially also contained in the reaction solution is not significantly damaged. A typical value for the denaturing temperature can be 95° C., for example. Preferably, heating the heating element to a temperature that is equal to or higher than the denaturing temperature can bring the advantage that the extracted nucleic acid at least partly becomes detached from the extraction nucleic acid and freely passes into the reaction solution. This can be advantageous, for example, when subsequently amplifying the extracted nucleic acid and/or if the extracted nucleic acid is to be removed or separated from the heating element.

The reaction solution is preferably a liquid in which the extracted nucleic acid as such can survive and/or is stabilized as a single strand and/or a double strand in the present case. However, the reaction solution differs from the sample liquid. In other words, the reaction solution is preferably designed such that the extracted nucleic acid is not damaged by the interaction with the reaction solution. For example, the reaction solution can be provided as an aqueous solution and/or as a buffer solution. If the intention is to amplify the extracted nucleic acid once it has been extracted, the reaction solution can preferably be designed such that the reaction solution allows such an amplification solution to be carried out. For example, the reaction solution can be in the form of a buffer solution in which it is possible to carry out a PCR in order to at least partly copy the extracted nucleic acid. The reaction solution is preferably provided in a reaction vessel. The reaction solution provided preferably has a volume of at least 1 µl and no more than 10 ml, more preferably of at least 5 µl and no more than 1 ml, most preferably of at least 10 µl and no more than 100 µl.

The invention provides the advantage that the heating element can be used directly for extracting the nucleic acid to be extracted from the sample liquid, by the heating element being provided with the at least one extraction nucleic acid. In other words, according to the invention the nucleic acid is preferably extracted from the sample liquid directly on the heating element, in particular on the surface thereof and in its immediate surroundings. Preferably, the heating element can thus be used to provide hybridization conditions, in particular a suitable hybridization temperature, in the immediate surroundings of the heating element.

The invention further provides the advantage that the extracted nucleic acid(s) is/are already bound to the heating element following the extraction. This makes it possible to carry out an amplification reaction, e.g. a PCR, after the extraction, using the heating element. The time required to extract and amplify the extracted nucleic acid can thereby be reduced. In particular, it is not strictly necessary according to the invention for the extracted nucleic acid to be first separated or removed again from the extraction substrate, i.e. according to the invention from the heating element, before carrying out an amplification reaction; instead, according to the invention the extracted nucleic acid can remain on the heating element. The beginning and/or course of a subsequent amplification reaction can thereby, for example, be significantly accelerated by using the heating element since the extracted nucleic acid is already arranged in the reaction solution volume or spatial region that can be locally heated by the heating element. It should be noted that, according to the invention, it is not strictly necessary for the nucleic acid to remain on the heating element following the extraction, but this may be particularly advantageous for the aforementioned reasons.

The invention further provides the advantage that the heating element, which can also be suitable for and/or designed to carry out an amplification reaction, can also be used to extract the nucleic acid from a sample liquid and thus for concentrating the nucleic acid to be extracted and optionally amplified. Particularly preferably, the device is designed to carry out an amplification reaction to copy the nucleic acid extracted from the sample liquid, wherein the heating of the heating element is preferably effected such that only an area immediately surrounding the heating element is locally heated at least to the denaturing temperature. Advantages of locally heating parts of a reaction solution when carrying out an amplification reaction are explained in DE102012201475A1, for example. Since the nucleic acid to be extracted can bind to the heating element via the extracted nucleic acid when the heating element is brought into contact with the sample liquid, once the extraction is complete the remaining sample liquid can be separated from the heating element, wherein the nucleic acid remains bound to the heating element. The heating element and the extraction nucleic acid bound thereto can thus serve to purify or concentrate the nucleic acid to be extracted, which can also be referred to as the target nucleic acid. As a result, the invention firstly allows the nucleic acid to be concentrated or purified or extracted, and secondly allows the extracted nucleic acid to be amplified. There is thus no need to provide separate devices for purification and amplification since, according to the invention, the device according to the invention can be used for both method steps.

In other words, the invention may provide the advantage that a device that is actually designed for amplification can also serve to purify or concentrate the nucleic acid to amplified by using a method according to the invention and/or by being designed as a device according to the invention.

The invention further provides the advantage that the sample liquid in which the nucleic acid to be extracted is provided can preferably also contain substances that are detrimental to amplification of the nucleic acid to be extracted. Since the sample liquid is separated from the heating element again after the nucleic acid has been extracted, all that preferably remains on the heating element is any nucleic acid extracted from said liquid, with the result that the substances that may impair the amplification are also extracted again from the heating element. There is thus no need to consider the needs and/or requirements of any subsequent amplification reaction when providing the sample liquid. Instead, the nucleic acid to be extracted (and amplified) can for example be provided in the form of a non-purified sample, for example of blood and/or mucus and/or bodily secretions, whereby the time required for the purification and amplification and the necessary effort can be reduced.

The invention may also provide the advantage that dilution of the sample liquid for the extraction and/or for an optional subsequent amplification of the nucleic acid from the sample liquid is not strictly necessary, and thus no detrimental reduction in concentration need be accepted. Since the extraction can take place using an undiluted sample liquid, the sensitivity of the nucleic acid detection can be significantly increased.

Alternatively or additionally, the invention may provide the advantage whereby one or more substances that can assist the extraction but can also optionally hinder any subsequent amplification can be added to the sample liquid and/or one or more such substances may already be contained in the sample liquid. For example, substances that promote binding or hybridization of the nucleic acid being extracted from the sample liquid to the extraction nucleic acids can be added to the sample liquid in order to increase the yield of extracted nucleic acid, for example, even if the presence of such substances would be disadvantageous during an amplification reaction, for example the presence of high sodium chloride or magnesium chloride concentrations and/or lysis buffers which may comprise lysis enzymes and/or chaotropic salts, for example. Since the sample liquid, apart from the nucleic acid extracted therefrom, is again separated from the heating element, when the heating element is subsequently used in an amplification reaction the substances that are disadvantageous for the amplification are no longer present in the reaction solution and can thus no longer disrupt the amplification reaction. The invention thus makes it possible to optimize the sample liquid for the extraction and, independently thereof, to optimize the reaction solution for amplifying the extracted nucleic acid. In a preferred embodiment, after the sample liquid has been removed, the heating elements are washed once or several times using a washing solution that is suitable for removing substances that can be detrimental to a PCR reaction while at the same time not influencing the bond between the extraction nucleic acid and the nucleic acid to be extracted. A washing solution of this kind can comprise or consist of a buffer solution containing e.g. $MgCl_2$ and/or NaCl.

The invention further provides the advantage that, in particular during the extraction and/or during an optional amplification of the nucleic acid, the sample liquid and/or the reaction solution can also be warmed or heated overall, i.e. the entire sample liquid or reaction solution as required, by means of the heating element. This can for example promote an at least partial hybridization of the nucleic acid being extracted with the extraction nucleic acid. Alternatively or additionally, such overall heating of the sample liquid and/or the reaction solution can also be used to at least partly denature the nucleic acid to be extracted, which may be advantageous in particular when the nucleic acid to be extracted is not or is not only present in single-strand form. Optionally, the sample liquid can also be heated as required by means of the heating element in order to lyse or break down and/or kill or deactivate micro-organisms in the sample liquid, and to provide access to any nucleic acids contained therein that are to be extracted, for example.

Preferably, the device for extracting the nucleic acid further comprises a reaction vessel. Particularly preferably, the heating element is connected to the reaction vessel and/or is formed as part of the reaction vessel. More preferably, the heating element is arranged in the reaction vessel such that the heating element extends preferably entirely or almost entirely, but at least partly, through a reaction volume at least partly enclosed by the reaction vessel. This provides the advantage that the sample liquid from which the nucleic acid is to be extracted and/or the reaction solution can thereby be brought into contact with the heating element particularly simply by filling the sample liquid or reaction solution into the reaction vessel.

Preferably, the heating element is heated such that only the heating element and an area immediately surrounding the heating element are heated to the denaturing temperature or to a higher temperature at which preferably the nucleic acid bound to the extraction nucleic acid preferably at least partly melts and/or denatures. Particularly preferably, only the immediate surroundings of the heating element(s) are locally heated for a short time up to the denaturing temperature or a higher temperature, whilst the majority of the reaction volume remains at a base (in the sense of "overall") temperature. For example, the base temperature can also be set during an optional subsequent amplification and can be such that, at the base temperature, elongation and/or hybridization (i.e. annealing) can preferably take place. Preferably, in this case a base temperature can optionally also be set by a separate heating device, wherein the base temperature determines a reaction solution temperature that the reaction solution assumes at least when is no heat input into the reaction solution is effected by means of the heating element. The heating device for controlling the temperature of the reaction solution to the base temperature can be positioned outside the reaction volume, for example, and can be designed to keep the temperature of the reaction solution at the base temperature as constant as possible. For example, the base temperature can be at least 55° C. and/or at most 70° C. Alternatively or additionally, it is also possible to provide a cooling device that can remove heat from the reaction solution whenever this is necessary to reach the base temperature. Whilst, according to preferred embodiments, the temperature of the reaction solution is brought to the base temperature by an (external) heating device such as a heating block, the heating element(s), which are at least partly but preferably largely or entirely located in the reaction solution, may for example only heat up at least a part of the reaction solution to the denaturing step.

According to other preferred embodiments, however, the heating element(s) can be used to control the temperature of the reaction solution to the base temperature and/or can support the heating of the reaction solution to the base temperature at least partly and/or at least temporarily. According to still other preferred embodiments, the temperature of the reaction solution can be controlled to the base temperature entirely or solely by the heating element(s), and so optionally there may be no need to provide an (external) heating device.

Furthermore, a device according to a preferred embodiment can comprise a heatable cover which can be used, for example, to seal a reaction vessel in which the reaction solution is contained. The cover can be heated to a temperature that is preferably a few degrees Celsius above the reaction solution temperature in order to at least partly prevent at least partial condensation of a vaporous proportion of the reaction solution on the cover.

Heating the heating element such that only the heating element and the immediate surroundings of the heating element are heated to the denaturing temperature or a higher temperature at which the nucleic acid bound to the extraction nucleic acid preferably at least partly melts and/or denatures, can be achieved, for example, by applying brief electrical pulses to the heating element, which is designed for example as a resistive heating element. In particular, this can preferably be achieved by the duration of the heating by the heating element being so short that the thermal field produced in the surrounding reaction volume, i.e. in the immediate surroundings, can only spread a few micrometres and thus creates a heating zone that preferably comprises only a tiny fraction of the reaction volume. In other words, the heating elements and their immediate surroundings are preferably heated so quickly that the heat cannot spread throughout the solution, and the solution, apart from the immediate surroundings of the heating elements, therefore remains substantially at the base temperature.

For this purpose, the heating element is heated particularly preferably for less than 100 ms, quite particularly preferably for less than 10 ms and quite particularly preferably for less than 1 ms, in order to ensure that during these heating periods, the temperature fields can spread less than preferably 100 µm, particularly preferably less than 35 µm and very particularly preferably less than 10 µm from the heating elements into the reaction solution by diffusion. The diffusion range x(t) of the heat in water can be quantified as a function of time (t) using the following relationship:

$$x(t) \approx \sqrt{10^{-7} \frac{m^2}{s} \cdot t}$$

Since the heating element(s) can preferably give off the heat to their surroundings very effectively due to their thermal conductivity properties and a maximum possible surface area-volume ratio, it can be achieved that the nucleic acids bound to their surface are exposed to a temperature field that is more than 5° C. hotter than the combined annealing and elongation temperature, which was set previously and will be set again following the denaturing step, preferably only for a brief denaturing period of preferably less than 100 ms, quite particularly preferably less than 10 ms and quite particularly preferably less than 1 ms. Particularly preferably, when the immediate surroundings of the heating elements are heated locally in this manner, there is no substantial overall heating of the reaction solution as a whole, i.e. the average temperature of the reaction solution preferably does not undergo any substantial temperature rise. Preferably, the temperature rise of the average temperature of the reaction solution per heating process by means of the heating element(s) is no more than 5° C., further preferably no more than 3° C., even further preferably no more than 1° C., more preferably no more than 0.5° C., much more preferably no more than 0.25° C. and most preferably no more than 0.1° C. Optionally, the temperature rise of the average temperature of the reaction solution per heating process by means of the heating element(s) is no more than 0.05° C. or no more than 0.01° C. Particularly preferably, the heating of the heating element comprises at least one heating process and is preferably effected such that the heating of the heating element per heating process and/or across all the heating processes increases an average temperature of the reaction solution by no more than 5° C., preferably by no more than 3° C., further preferably by no more than 1° C., more preferably by no more than 0.5° C., much more preferably by no more than 0.25° C., most preferably by no more than 0.1° C. A heating process here comprises heating the heating element to a temperature that is equal to or higher than a denaturing temperature of the nucleic acid bound to the extraction nucleic acid.

This provides the advantage that the immediate surroundings of the heating element can be heated with particularly low energy and heat input and/or that the temperature in the immediate surroundings of the heating element can be changed particularly rapidly and/or lowered again particularly rapidly. In particular, due to rapid thermalization of the reaction solution following the heating, the temperature gradients formed during the heating can be dissipated again very rapidly, which allows a very short duration of a thermal cycle.

In particular, the amount of heat input can thus be so low that no substantial overall heating of the reaction volume, i.e. of the entire reaction solution takes place. The "overall temperature" within the meaning of the present invention is the average temperature of the reaction volume or reaction solution based on the capacity or the entire reaction solution, i.e. the temperature that, following thermalization of the reaction volume, is or would be set therein. The "overall heating" is the increase in the overall temperature thus defined. This makes it possible to reduce the amount of energy to be supplied to the reaction solution in order to reach the denaturing temperature in the immediate surroundings of the heating element, whereby the energy and also the time requirement can be minimized.

In addition, this provides the advantage that, once the immediate surroundings of the heating element have been heated, the input heat that spreads from the heating zone into the rest of the reaction volume only gives rise to a negligible overall temperature increase there. "Negligible" here means in particular that the temperature increase is preferably too low for denaturing of the nucleic acid molecule and, particularly preferably, that the temperature increase is too low to disrupt the hybridization and elongation. The denaturing, and optionally also other steps of any nucleic acid copying using the heating element to which the extracted nucleic acid is bound, can thus take place locally in the immediate surroundings of the heating elements. Furthermore, an optionally desired melting and/or denaturing of the (extracted) nucleic acid(s) bound to the heating element via the extraction nucleic acid can be carried out particularly rapidly and/or with particularly low energy input and/or with particularly low overall heating of the reaction solution.

Since, during local heating by means of the above-specified brief heat pulses, the input thermal energy is initially distributed only to the heating elements and can initially only diffuse a few micrometres into the reaction solution, the amount of heat input is distributed to a very small fraction of the entire reaction solution. Since this initial heating zone contains the nucleic acids that are to be thermally denatured and in particular are at least partly bound to the surface of the heating elements, sufficient heating for denaturing can be achieved in the comparatively small volume of the heating zone with a small amount of energy. However, as soon as this input amount of energy is distributed to the much larger remainder of the reaction solution, the heating zone cools down and the entire reaction solution warms up to an extremely small degree, preferably to a negligible degree.

Particularly preferably, the energy input into the reaction solution via the heating elements in a denaturing step is less than the energy required to heat the entire reaction solution by preferably 5° C. or particularly preferably 3° C. and quite particularly preferably 2° C.

In other words, due to the local heating, denaturing of the extracted nucleic acid close to the heating elements is achieved and at the same time the overall heating of the reaction solution is restricted to a small and/or negligible degree compared with the temperature before the beginning of the dehybridization step. This is a further advantage over conventional PCRs, in which in each denaturing step it is necessary to input an amount of energy that typically causes a (an overall) temperature increase in the reaction solution of >20° C. (for example, in order to bring the reaction solution from the elongation temperature of 72° C. to the dehybridization temperature of 95° C.). The energy required to cause a particular temperature increase in the reaction solution can be calculated from the heat capacity of the reaction solution (and the heat capacity of the heating elements unless this is supposed to be negligible) since both the specific heat capacity of the preferably aqueous reaction solution and its mass are known to the experimenter. The energy actually dissipated in the reaction solution (and not, for instance, in the supply lines and/or reaction vessel) is to be taken into account.

Preferably, the reaction solution is designed to carry out an amplification reaction to copy at least a part of the extracted nucleic acid in the reaction solution. This provides the advantage that the heating element can be used for extraction of the nucleic acid and also for amplification of the nucleic acid. It is thus not strictly necessary to have two separate devices in which the nucleic acid has to be separately extracted or concentrated first and only then can the nucleic acid be amplified in another device. In particular, this makes it possible to add the reaction solution for the amplification reaction to the extracted nucleic acid bound to the heating element and to carry out an amplification reaction. Particularly preferably, this can be effected without the reaction solution being polluted and/or contaminated by the sample liquid. In particular, it is not necessary to mix some of the sample liquid into the reaction solution (apart from the nucleic acid bound to the heating element). Rather, it is thereby made possible to transfer the nucleic acid bound to the heating element into the reaction solution by means of the heating element in extracted form, i.e. preferably without any residues of other components of the sample liquid. This further provides the advantage that the extracted nucleic acid to be amplified is already bound to the heating element and can thus be heated to the denaturing temperature directly by means of local heating. In other words, the amplification can proceed as part of the amplification process directly together with the heating of the nucleic acid to be amplified up to the denaturing temperature.

Preferably, the heating of the heating element is effected within the context of the amplification reaction for copying at least a part of the extracted nucleic acid and is preferably repeated at least once. In particular, the amplification reaction can preferably comprise or be designed as a polymerase chain reaction. The amplification reaction can comprise several cycles that are run through in order to amplify the nucleic acid, and preferably can comprise several heating steps in which the heating element heats the reaction solution at least partly and at least temporarily, in particular locally, to a predefined temperature. It is particularly advantageous if the nucleic acid to be amplified is provided already bound to the heating element, since the heat provided by the heating element can thus act on the nucleic acid being amplified directly and immediately, preferably once the extraction nucleic acid (which here serves as a primer) has been elongated by a polymerase.

Preferably, at least one primer for the amplification reaction is bound to the heating element. Alternatively or additionally, the at least one primer is provided such that the at least one primer binds to the heating element. In other words, at least one of the required primers is secured to the heating element (referred to hereinafter as "functionalized"). This provides the advantage that the amplicon can also be produced at this site and thus denaturing is made possible with local heating. In other words, since the PCR steps, in particular the hybridization, elongation and/or denaturing, and preferably also the generation of a signal for observing the progress of the PCR are located in the immediate vicinity of the heating apparatus due to the heating apparatus having been functionalized, the heating of the reaction volume can be restricted to a fraction of the reaction volume.

In particular, this provides the advantage that nucleic acids can be copied more rapidly than with conventional methods, in which the entire reaction solution has to be heated, i.e. in which overall heating must be effected. In particular, unlike conventional thermocycles in which the heating and cooling processes last several seconds, the invention makes it possible for the duration of the amplification reaction to no longer be determined by technical limitations such as heating and cooling rates. There are also no longer any thermalization times in the reaction vessel since the heat is always generated in the surroundings of the heating apparatus. Even with 40 runs of the copying cycle of a PCR, it takes a total of less than one second to denature the nucleic acid molecule and cool it to an elongation and hybridization temperature. It can thereby be achieved that the duration of the PCR can be determined mainly by the period of time between the denaturing steps that the polymerase requires for diffusion and reaction processes and the biochemical processes, such as elongation. This further provides the advantage that nucleic acids are copied with lower energy consumption than in conventional methods. In addition, the copying process can be more effectively controlled and, for example, the reaction volume temperature overshoot and undershoot that often occur in conventional methods during the temperature control can be largely avoided.

Additionally, it is thus possible to provide cost-effective and compact devices that can be used for extracting or purifying the nucleic acid and also for copying the nucleic acid. For example, it is preferably possible to provide a device of this kind for copying nucleic acids in the form of a Universal Serial Bus (USB) stick.

Preferably, the extraction nucleic acid is designed as a primer for the amplification reaction. This provides the advantage that the same nucleic acid which can be formed as an oligonucleotide for example, can be used for both extracting and amplifying the nucleic acid. This further provides the advantage that it may be sufficient to functionalize the heating element with only one type of extraction nucleic acid, which can then serve as both an extraction nucleic acid and a primer. Additionally, this provides the advantage that, when the heating element is heated, which may take place as early as in the first cycle of the amplification reaction, the nucleic acid to be amplified is already bonded to the primer and is arranged in the immediate surroundings of the heating element, which are locally heated. The amplification reaction can thus begin and/or be carried out particularly rapidly.

Preferably, a plurality of heating elements are provided. In other words, preferably multiple heating elements are provided. In other words, at least two heating elements are provided, wherein each of the plurality of heating elements preferably has the properties and/or functions described. Preferably, a plurality of extraction nucleic acids are provided. In other words, preferably multiple extraction nucleic acids are provided, wherein the heating element or the plurality of heating elements are each preferably bonded to several extraction nucleic acids and/or wherein the one or more extraction nucleic acids are provided so as to bind to the heating element or plurality of heating elements. The plurality of heating elements can be provided having different extraction nucleic acids, wherein each heating element can be provided with similar extraction nucleic acids and the extraction nucleic acids differ between the various heating elements and/or wherein at least one or some of the heating elements are each provided with different extraction nucleic acids. Particularly preferably, a plurality of heating elements are provided, which are each functionalized with a plurality of extraction nucleic acids. Preferably, a heating element is functionalized with at least 10, more preferably at least 1,000, even more preferably at least 100,000, most preferably at least 1,000,000 extraction nucleic acids. Preferably, one or more or all of the plurality of heating elements are functionalized with extraction nucleic acids such that they have a surface density of at least 0.001 extraction nucleic acid molecules per square nanometre, particularly preferably of at least 0.01 extraction nucleic acid molecules per square nanometre, and quite particularly preferably of at least 0.1 extraction nucleic acid molecules per square nanometre. This can provide the advantage that efficient reaction kinetics are possible. At the same time, the surface density on the surface of the heating element is preferably less than 100 extraction nucleic acid molecules per square nanometre, particularly preferably less than 10 extraction nucleic acid molecules per square nanometre and quite particularly preferably less than 1 extraction nucleic acid molecule per square nanometre. This can provide the advantage that good accessibility and/or low steric hindrance is possible during the hybridization of the nucleic acid to be extracted.

Preferably, the heating element is arranged in a reaction vessel and is preferably mechanically connected to the reaction vessel. Alternatively or additionally, the heating element is formed as part of the reaction vessel. This provides the advantage that the heating element can be brought into contact with the sample liquid and/or with the reaction solution by at least partly filling the reaction vessel with the sample liquid or with the reaction solution so that the heating element is at least partly covered by the sample liquid or by the reaction solution. Additionally, separating the heating element from the sample liquid may comprise removing the sample liquid from the reaction vessel. Preferably, the reaction vessel has at least one opening for filling the sample liquid into the reaction vessel and/or for removing the reaction solution from the reaction vessel. For example, the sample liquid can be suctioned out of the reaction vessel. In other words, bringing the heating element into contact with the sample liquid comprises at least partly filling the reaction vessel with the sample liquid, and/or separating the heating element from the sample liquid comprises at least partly removing the sample liquid from the reaction vessel. In particular, the reaction vessel can be equipped with a feed line and/or a drain, via which the sample liquid and/or the reaction solution and/or any other liquids or reagents can be filled into the reaction vessel or drained from the reaction vessel. This thus provides the advantage that the heating element can be brought into contact with and/or separated from the sample liquid and/or the reaction solution particularly simply. This further provides the advantage that the heating element is arranged in a reaction volume, i.e. in the volume that the reaction solution then at least partly occupies, and the heating element is in contact with and can interact with the reaction solution even after the nucleic acid has been extracted.

For example, the method for extracting the nucleic acid from the sample liquid can then comprise providing a reaction vessel to which an extraction nucleic acid arranged in the reaction vessel is bonded, wherein the extraction nucleic acid is at least partly complementary to the nucleic acid to be extracted from the sample liquid. The method can further comprise filling the reaction vessel with the sample liquid in such a way that the extraction nucleic acid is covered with the sample liquid and the nucleic acid to be extracted from the sample liquid can bind to the extraction nucleic acid, as well as removing the sample liquid from the reaction vessel in such a way that the nucleic acid bound to the extraction nucleic acid at least partly remains in the reaction vessel.

In other words, bringing the heating element into contact with the sample liquid preferably comprises wetting the heating element with the sample liquid and/or immersing the heating element in the sample liquid and/or at least partly filling the reaction vessel with the sample liquid.

Preferably, the method further comprises cleaning the reaction vessel after separating the heating element from the sample liquid, wherein cleaning the reaction vessel comprises removing residues of the sample liquid from the reaction vessel. For this purpose, for example, a washing solution can be used, which is brought into contact with the heating element and/or with the reaction vessel in order to remove any residues of sample liquid from the heating element and/or from the reaction vessel. The cleaning may comprise one or more washing processes, i.e. the heating element can be brought into contact with one or more washing solutions once or several times. For example, the washing solution(s) can be filled into or drained from the reaction vessel through the feed line and the drain, respectively, if the reaction vessel comprises these. Alternatively or additionally, the heating element can be immersed in and/or sprayed with and/or flushed with one or more washing solutions. This provides the advantage that any sample-liquid residues, which could disrupt any amplification reaction in the reaction solution, can be reliably removed.

Preferably, the heating element has an electrically conductive body which, perpendicular to the direction of flow, preferably in one spatial direction and particularly preferably in every spatial direction perpendicular to the direction of flow, has an extension R that preferably measures at least 0.2 μm and at most 0.5 mm. Further preferably, the extension R measures at least 0.2 μm and at most 0.3 mm, more preferably at least 0.5 μm and at most 200 μm, much more preferably at least 1 μm and at most 100 μm, particularly preferably at least 2 μm and at most 50 μm, and quite particularly preferably at least 5 μm and at most 30 μm. This provides the advantage that, by means of one or more heating elements dimensioned in this way, a suitable heat input into the reaction solution can be achieved, and also the heating element(s) is/are sufficiently stable and/or robust to withstand processing and/or use as a heating element.

However, if smaller values than the minimum values stated are selected for the extension R perpendicular to the direction of flow, this can result in structures that are too delicate for processing or production thereof. By contrast, if excessively high values are selected, this can result in the heating elements inputting too much heat into the solution when they are energized, since they would have a surface area-volume ratio that is disadvantageous for the intended use. According to preferred embodiments, the heating element(s) can be designed as heating wire(s) and can preferably have round and/or polygonal and/or oval cross-sectional shapes. According to other preferred embodiments, however, it is also possible to use different-shaped heating wires that are energized in the longitudinal direction and the diameter or circumferential diameter of which corresponds to the dimension R. According to another preferred embodiment, the heating element(s) can have a honeycomb structure. For example, a metal foil into which the desired honeycomb structure(s) is/are etched can be used to produce (a) heating element(s) of this kind. Heating elements having a large surface area-volume ratio can also be applied to suitable substrates using printing techniques (e.g. screen printing of conductive structures) and thick-film methods.

This provides the advantage that the heating wire has a particularly large surface area in relation to its volume. By means of as large a surface area as possible in relation to volume, the surface area in contact with the sample liquid can be particularly large, with the result that efficient heating of the reaction solution is made possible. Furthermore, the large surface area allows significant loading with extraction nucleic acids and/or other nucleic acids, such as oligonucleotides and/or primers, in order to allow nucleic acid to be reliably extracted from the sample liquid and/or to allow the nucleic acid to be reliably amplified on the heating element. In addition, the heat capacity of the heating element is thus minimized while having as large a surface area as possible in order to minimize the slowness when heating and cooling the heating element, thereby making it possible to achieve very rapid and pronounced temperature gradients; this is very advantageous in particular for locally heating the immediate surroundings of the heating element.

Preferably, the device does not have only one heating element, but a plurality of heating elements. These can be formed similar and/or different. Furthermore, these can be formed separately or contiguously. In particular, the heating elements can be arranged such that electrical voltage and/or current can be applied to them together and/or electrical voltage and/or current can be applied to them separately. For example, the heating elements can at least partly form a heating apparatus. For example, the plurality of heating elements can be formed as an arrangement and/or a mesh and/or a web of wires. This provides the advantage that the extraction of the nucleic acid from the sample liquid and/or the heating or local heating of the reaction solution can be improved since the contact area between the sample liquid or reaction solution and the plurality of heating elements can be made larger than when there is only one heating element.

It is preferred that the heating elements have as high a surface area-volume ratio (SVR) as possible in order to allow the heat to be given off to the (immediate) surroundings as effectively as possible while at the same time having as low a volume as possible in order to ensure a low heat capacity of the heating element. Preferred embodiments have an SVR for the heating elements of more than $10^3$ m$^{-1}$ (per metre), preferably more than $10^4$ m$^{-1}$, and particularly preferably more than $5*10^4$ m$^{-1}$. However, too great an SVR can in some cases lead to very delicate and thus mechanically unstable structures, and so it may be advantageous to keep the SVR preferably less than $10^9$ m$^{-1}$, particularly preferably less than $10^8$ m$^{-1}$ and most preferably even less than $10^7$ m$^{-1}$.

For example, the heating element may have a long wire and/or a thin film and/or a foil preferably having a suitable SVR. For a long wire (length much greater than diameter), the SVR is calculated, for example, by 2/r, wherein r is the radius of the wire. For a thin film or a foil (thickness very much smaller than length and lateral extension), the SVR is calculated by 1/d, wherein d is the thickness of the film or foil. For the above embodiments, it is preferable according to the invention to consider only the surface area in contact with the reaction volume; in addition, only the volume the surface area(s) of which is/are in contact with the reaction volume is preferably to be considered (this means, for example, that supply lines that do not run through the solution are not to be considered as relevant volumes and surface areas according to the invention). The same also applies, mutatis mutandis, to the subsequent consideration of volume fill factor and heat capacity.

In a preferred embodiment of the invention, the ratio between the surface area of the heating elements that is in contact with the reaction volume and the reaction volume, is greater than 0.1 m$^{-1}$, particularly preferably greater than 1 m$^{-1}$, particularly preferably greater than 5 m$^{-1}$, particularly preferably greater than 10 m$^{-1}$, particularly preferably greater than 20 m$^{-1}$, particularly preferably greater than 50 m$^{-1}$, particularly preferably greater than 100 m$^{-1}$. With this embodiment of the invention, favourable reaction kinetics can advantageously be achieved in that, in a large part of the reaction volume, constituents of the reaction volume are able, by diffusion, to rapidly reach the surface of a heating element, in order to participate in the nucleic acid copying steps taking place there. In the case of heating elements that are at least partly functionalized with one of the primers on their surface, as described elsewhere, it is also possible to exploit the fact that even more reaction partners are available due to a larger surface area.

In order to prevent the heating element structure from becoming too delicate or to prevent the movement of the nucleic acids or nucleic acid molecules and/or other reactants contained in the reaction volume from being hindered by too many surfaces, the ratio of the surface area of the heating element(s) in relation to the size of the reaction volume is preferably less than $10^6$ m$^{-1}$, more preferably less than $10^5$ m$^{-1}$, much more preferably less than $10^4$ m$^{-1}$ and quite particularly preferably less than $10^3$ m$^{-1}$.

In order to keep the heat supplied by the heating element supplies to the reaction volume in the denaturing step as low as possible, it may be advantageous to also keep the heat capacity of the heating elements low since the greater the heat capacity of the heating element, the greater the amount of energy required to achieve a particular temperature increase on the surface of the heating elements. The amount of energy supplied by the heating elements to the reaction volume in the denaturing step then spreads to the entire reaction volume. The heat capacity of the heating element is calculated from the product of the respective volume and the specific volumetric heat capacity of the respective material of which the respective volume consists. There is a substantial degree of freedom in the design of the heating elements in terms of their dimensions. It may therefore be advantageous to keep the volume of the heating element, in particular the material thickness, as low as possible. It is noteworthy here that the heat diffusion range is dependent not on the size of the heating element, but only on the duration of heating. In a preferred embodiment of the invention, the volume of all the heating elements or of the heating element is less than 10%, preferably less than 5%, particularly preferably less than 3% and quite particularly preferably less than 1% of the reaction volume. In this design of the invention, a low heat capacity of the heating elements can be achieved by a low volume fill factor.

Preferably, the at least one extraction nucleic acid is bound to the heating element directly and/or is bound to the heating element indirectly via an adapter nucleic acid. Alternatively or additionally, the heating element comprises at least one adapter nucleic acid, via which the extraction nucleic acid binds to the heating element when the extraction nucleic acid is provided such that the extraction nucleic acid binds to the heating element. In other words, the extraction nucleic acid can bind to the heating element directly or indirectly via an adapter nucleic acid. For this purpose, the adapter nucleic acid can, for example, be firmly bound to the heating element and can be designed such that the extraction nucleic acid can at least partly hybridize with the adapter nucleic acid, for example by means of a binding portion of the nucleotide sequence, which preferably differs from another extraction portion. This provides the advantage that the adapter element can be designed having universal adapter nucleic acids and can be customized for the desired purpose in a simple manner by adding correspondingly designed extraction nucleic acids to the sample liquid.

Further advantages and embodiments of the invention will become apparent from the description and the accompanying drawings.

It goes without saying that the features mentioned above and still to be explained below can be used not only in the combination stated in each case, but also in other combinations or in isolation, without departing from the scope of the present invention.

The invention is schematically represented in the drawings with reference to embodiment examples and will be described below with reference to the drawings.

DETAILED DESCRIPTION OF THE DRAWINGS

Figure 1A:
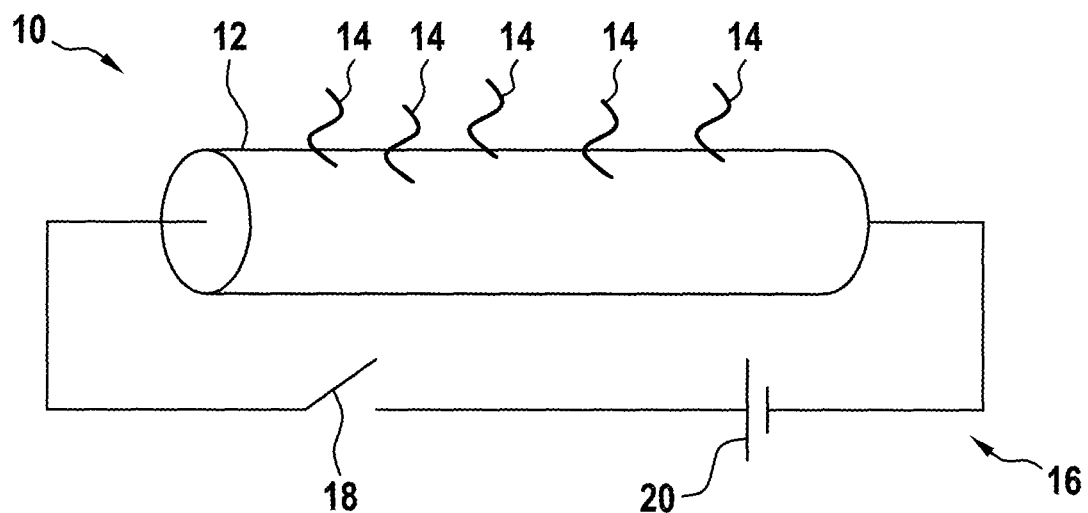
FIGS. 1A to 1D are schematic representations of heating elements according to two preferred embodiments.

FIG. 1A is a schematic representation of a heating element 10 according to a first preferred embodiment. The heating element 10 is in the form of a wire or heating wire 12 that has been functionalized with several extraction nucleic acids 14 on its surface. It should be mentioned here that the heating element 10 is only shown schematically and the heating element 10 actually used may have different dimensions and in particular a different length-to-diameter ratio.

The extraction nucleic acids 14 are in the form of oligonucleotides and, at least partly, have a nucleotide sequence that is at least partly complementary to the nucleotide sequence of at least a part of the nucleic acid to be extracted 22 from a sample liquid. For example, the extraction nucleic acids 14 can be bound to the surface of the heating element 10 by means of a thiol and/or sulphur bond. Preferably, the heating element 10 has a surface that promotes the binding of the extraction nucleic acids 14 to the heating element 10 or wire 12. For example, the heating element 10 or wire 12 can be made of a noble metal, such as gold, and/or at least partly be coated with gold on its surface in order to promote reliable binding of the extraction nucleic acids 14 to the heating element 10.

The heating element 10 has a power supply 16, by means of which the heating element 10 can be supplied with electrical voltage and/or electrical current in order to heat the heating element 10 and locally heat the immediate surroundings of the heating element 10, i.e. of the heated wire 12. Furthermore, the entire reaction solution surrounding the heating element 10 can optionally be heated overall, i.e. completely, as required, by means of the heating element 10. For example, an electrical voltage provided by the voltage source 20 can be applied to the heating element 10 by closing a switch 18, with the result that an electrical current flows through the heating element 10 in a controllable manner and heats it in a resistive manner. For example, the current can be provided in pulsed form in order to achieve as sharp a temperature gradient as possible, in terms of time and/or space, in a reaction solution in the immediate surroundings of the heating element.

Figure 1B:
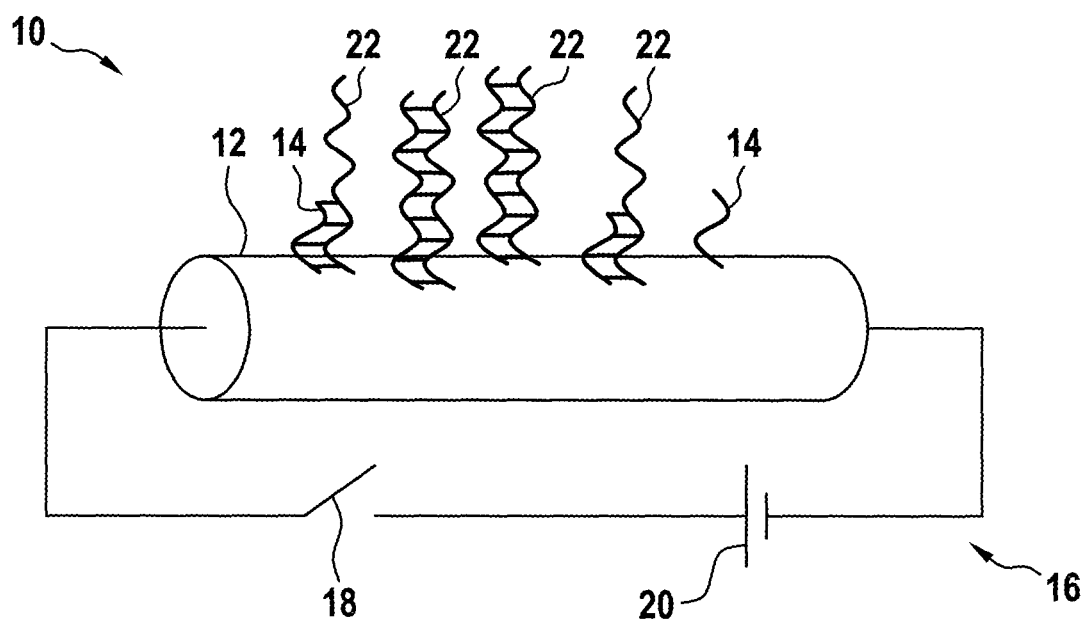

To extract the nucleic acid 22 to be extracted from a sample liquid, the heating element 10 can be at least partly covered with the sample liquid. For example, the heating element 10 can be at least partly immersed in the sample liquid and/or can have the sample liquid poured over it. If the nucleic acid 22 to be extracted is present, and preferably free, i.e. unbound, in the sample liquid, a single strand of the nucleic acid 22 can attach to an extraction nucleic acid 14 and hybridize therewith, unless the latter is already occupied by another nucleic acid. FIG. 1B shows the heating element from FIG. 1A to which nucleic acids 22 extracted from a sample liquid are bound. The nucleic acids 22 at least partly form double strands together with the extraction nucleic acids 14. According to a preferred embodiment, the heating element 10 can be used to provide a temperature in the immediate surroundings of the heating element 10 that is suitable for the nucleic acid 22 to hybridize with the extraction nucleic acid 14, in order to improve and/or accelerate the hybridization, for example.

If the nucleic acid 22 is bound to or hybridized with the heating element 10 via the extraction nucleic acids 14, the heating element 10 together with the nucleic acids 22 can be separated from the sample liquid again, wherein the nucleic acids 22 remain on the heating element 10. For example, the heating element 10 can be removed from the sample liquid if the heating element 10 has been immersed therein and/or the sample liquid can be decanted and/or suctioned away. One or more washing processes can also be carried out in order to remove as fully as possible any sample-liquid residues that may have been deposited on the heating element 10. However, in terms of the washing reagents or washing solutions and/or in terms of their execution, the washing processes are to be selected such that the nucleic acids 22 are still at least partly bound to the heating element 10 with the extraction nucleic acids 14 even after the washing processes.

Figure 1C:
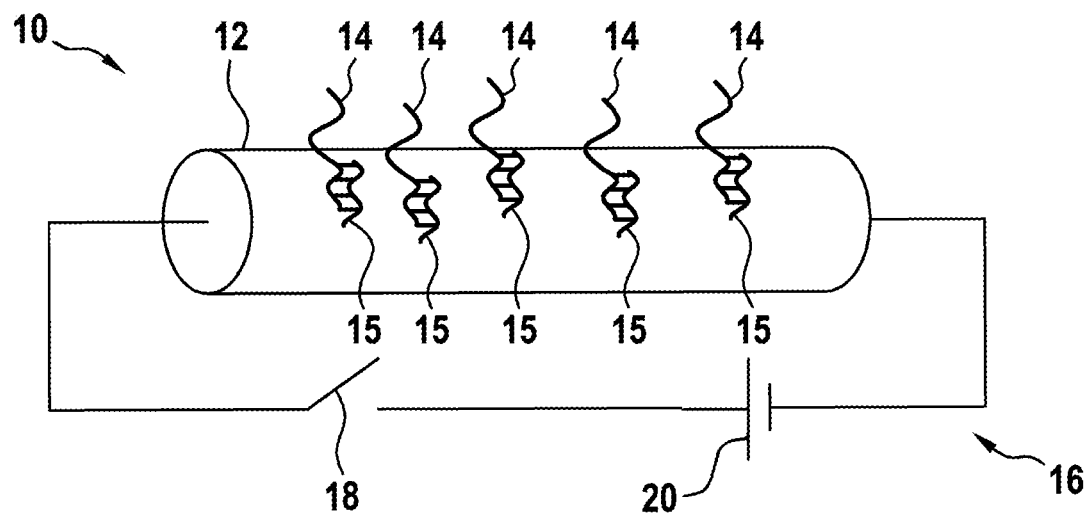
Figure 1D:
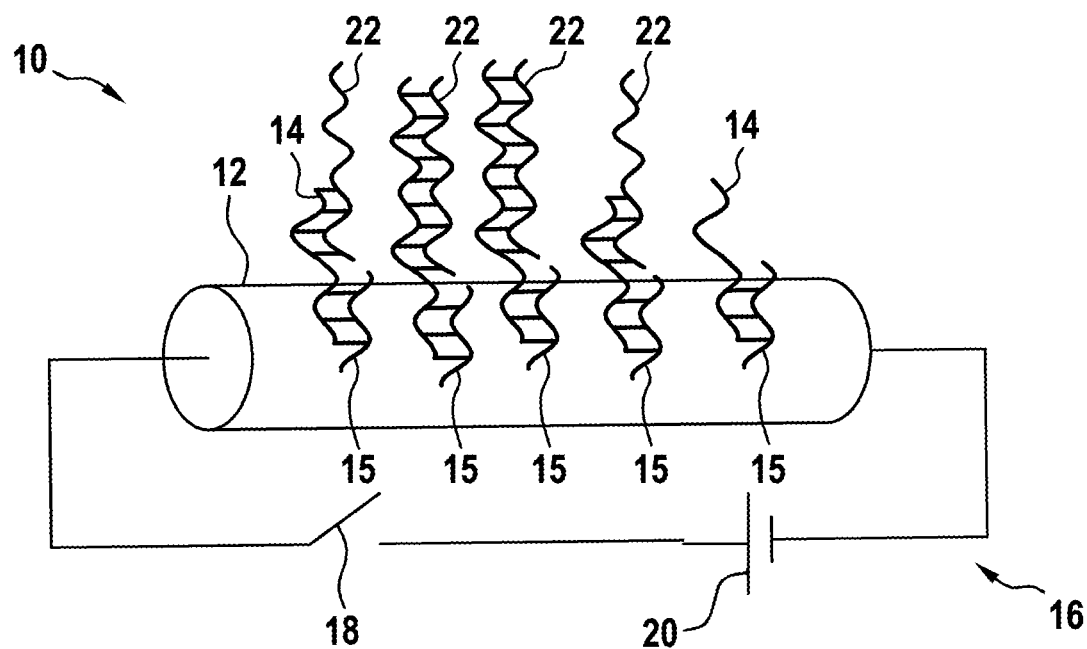

FIGS. 1C and 1D are schematic representations of a heating element 10 according to another preferred embodiment, which largely corresponds to the embodiment from FIGS. 1A and 1B but differs therefrom with respect to the functionalization using extraction nucleic acids 14. Whereas in the embodiment shown in FIGS. 1A and 1B, the extraction nucleic acids 14 are bound directly to the heating element 10, e.g. by means of a thiol bond, according to the second preferred embodiment shown in FIGS. 1C and 1D, the extraction nucleic acids 14 are bound to the heating element 10 indirectly via adapter nucleic acids 15. For example, the adapter nucleic acids 15 may be bound to the heating element 10 by means of a thiol bond. The extraction nucleic acids 14 can then hybridize with an adapter nucleic acid 15 and thus bind to the heating element 10 indirectly. For this purpose, the extraction nucleic acids 14 can preferably have a binding portion, via which the extraction nucleic acids 14 can hybridize with an adapter nucleic acid 15, and an extraction portion, by means of which the extraction nucleic acids 14 can bind to the nucleic acid to be extracted.

Figure 2A:
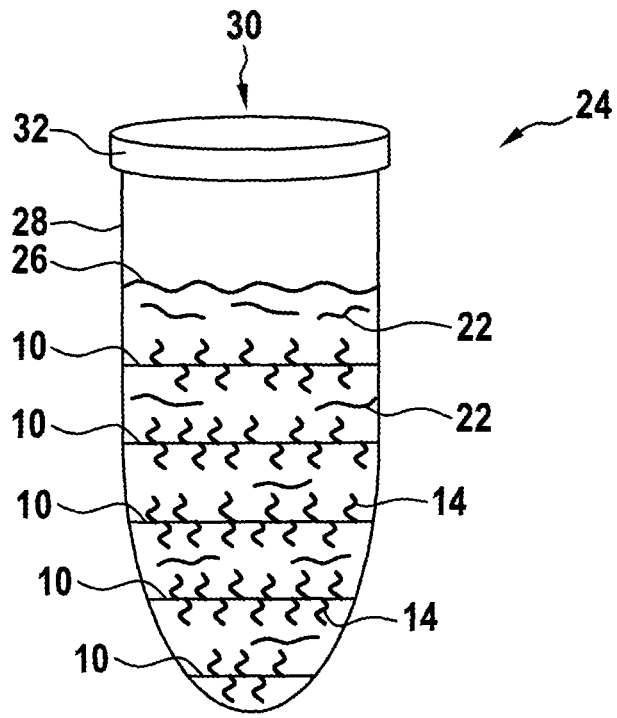
FIGS. 2A and 2B are schematic representations of a device according to preferred embodiments for extracting a nucleic acid from a sample liquid.

FIG. 2A is a schematic representation of a device 24 for extracting a nucleic acid 22 from a sample liquid 26. The device 24 has a reaction vessel 28, which encloses a reaction volume in which the sample liquid 26 and/or the reaction solution can be arranged. According to the representation in FIG. 2, the reaction vessel 28 is filled with the sample liquid 26 such that the heating elements 10 arranged in the reaction vessel 28 are covered by the sample liquid 26.

The heating elements 10 are firmly connected to the reaction vessel 28, i.e. the heating elements 10 remain in the reaction vessel during separation from the sample liquid. In particular, the heating elements 10 can be firmly connected to the reaction vessel 28 so that they preferably form a single-piece unit with the reaction vessel 28. Alternatively, the heating elements 10 can be formed separately from the reaction vessel 28 and can merely be arranged and optionally secured and/or anchored therein. The securing and/or anchoring can be permanent, i.e. not detachable, or detachable. According to preferred embodiments, the heating elements 10 can be electrically contacted via a vessel wall of the reaction vessel 28. Alternatively or additionally, the heating elements 10 can be electrically contacted via an opening 30 in the reaction vessel 28, which opening is closed with a cover 32 according to the embodiment shown. For example, bushings may be provided to allow for connection lines for contacting the heating elements 10 in the reaction vessel 28 even when the cover 32 is closed. For example, each heating element 10 can be supplied with electrical energy separately by means of its own voltage source (not shown) and/or all the heating elements 10 can be supplied with electrical energy via a shared voltage source (10).

The nucleic acids 22 to be extracted are at least partly free in the sample liquid 26. The conditions, in particular the temperature of at least part of the sample liquid 26, are selected such that at least some of the nucleic acids 22 in the sample liquid 26 at least partly hybridize to the extraction nucleic acids 14 and can thus each bind to a heating element 10. Once the hybridization is complete, the sample liquid 26 can be separated from the heating elements 10 and/or the reaction vessel 28 again. The separation can be carried out, for example, by the sample liquid 26 being poured and/or suctioned away out of the reaction vessel 28 once the nucleic acids 22 have had sufficient time to hybridize with the extraction nucleic acids 14. For example, a few seconds may be sufficient. Since the nucleic acids 22 are hybridized to the extraction nucleic acids, they remain on the heating elements 10 and thus in the reaction vessel 28 while and after the sample liquid 26 is separated.

Once the sample liquid 26 has been separated from the heating elements 10, i.e. for example once the sample liquid 26 has been poured and/or suctioned away, one or more washing steps can be carried out, for which purpose one or more washing reagents or washing solutions, for example, can be poured into the reaction vessel 28 to remove any residues of the sample liquid. However, the washing reagents and washing steps must be designed such that not all the nucleic acids 22 bound to the heating elements 10 are damaged and/or removed, but instead at least some of the nucleic acids 22, but preferably, all of the nucleic acids 22, remain intact and bound to the heating elements. This is particularly important in order to ensure that the nucleic acids 22 at least partly remain on the heating elements 10 when the one or more cleaning reagents are separated from the heating elements 10.

Once the nucleic acids 22 have been separated from the heating elements 10 and following the optional one or more washing processes, the heating elements 10 can be brought into contact with the reaction solution by the reaction solution being filled into the reaction vessel 28 in such a way that the heating elements 10 are at least partly, but preferably completely, covered with the reaction solution. Then, by heating at least some of the heating elements 10, but preferably all of the heating elements 10, the reaction solution in the immediate surroundings of the heating elements 10 can be heated to a temperature that is equal to or higher than the denaturing temperature, with the result that the nucleic acid 22 becomes detached from the extraction nucleic acid 14 and passes into the reaction solution in free form. In particular, this can serve the amplification of the nucleic acid 22. According to this preferred embodiment, however, the bonds of the extraction nucleic acids 14 to the heating element are selected such that the extraction nucleic acids 14 preferably do not become detached from the heating elements 10 even when the heating elements 10 are heated to the denaturing temperature or to a slightly higher temperature.

According to another preferred embodiment, however, the bonds of the extraction nucleic acids 14 to the heating element 10 can also be designed such that they are bound to the heating element 10 via an adapter nucleic acid, i.e. indirectly, for example. In particular, in order to bind to the heating element 10, the extraction nucleic acids 14 can hybridize with one or more adapter nucleic acids in order to then bind to the heating element via the one or more adapter nucleic acids. Preferably, the adapter nucleic acids are firmly bound to the heating element 10, for example by means of a thiol bond, and preferably remain firmly bound to the heating element 10 even while and/or after the heating element 10 is heated. According to these preferred embodiments, at least some of the extraction nucleic acids 14 bound indirectly to the heating element 10 can at least partly become detached from the adapter nucleic acid and thus from the heating element 10 while the heating element 10 is being heated. For example, this can occur due to an at least partial dehybridization of the extraction nucleic acids 14 from the adapter nucleic acid bound thereto. Even though the extraction nucleic acids 14 at least partly become detached from the heating element 10, i.e. at least some of the extraction nucleic acids 14 become detached from the heating element 10 and/or only some of the extraction nucleic acids 14 dehybridize from the adapter nucleic acid, the extraction nucleic acids 14 that have become detached from the heating element 10 may still be located close to the heating element 10 at the start of the next heating step, in which the heating element 10 is heated again, and/or may be bound again to the adapter nucleic acid to which the extraction nucleic acids 14 were previously bound, or may be bound to another extraction nucleic acid 14. This can be promoted in particular by the fact that no flow is actively generated in the reaction solution and/or the fact that the successive heating steps have only a small interval of for example a few seconds between them. For example, this can be achieved in that, despite at least some of the extraction nucleic acids 14 having become detached from the heating element 10, the extraction nucleic acids 14 that have become detached therefrom are still at least partly located in the spatial surroundings of the heating element 10 that are heated by the heating element 10.

To carry out the amplification of the nucleic acid 22 or nucleic acids 22, the reaction solution is preferably designed to be suitable to carry out the amplification reaction therein. For example, the amplification reaction can comprise or be designed as a polymerase chain reaction (PCR). In this case, the reaction solution can particularly advantageously be designed as a buffer solution for a PCR. The performance of the several thermal cycles within the context of the PCR, which comprise heating (at least part of) the reaction solution to a denaturing temperature and cooling said solution to a hybridization temperature, can be carried out locally in the immediate surroundings of the heating elements 10 by heating the heating elements 10 accordingly. Preferably, for this purpose at least one type of primer for the PCR is also functionalized to the heating elements 10 and/or bound to the heating element 10 or heating elements 10 via one or more adapter nucleic acids. Particularly preferably, at least some of the extraction nucleic acids 14 are formed as primers for the PCR and thus have the role of both extraction nucleic acid and primer. In addition, identical and/or different primers can be free within the reaction solution and/or can be functionalized to the heating element(s) 10 and/or can be bound to the heating element 10 or heating elements 10 indirectly via one or more adapter nucleic acids.

For example, the first run of the PCR copying cycle can proceed as follows: The nucleic acids hybridized to the primers (preferably in the form of forward primers) or extraction nucleic acids 14 are elongated by means of a polymerase provided in the reaction solution, whereby, with respect to the nucleic acid 22 that represents the target nucleic acid, due to the lengthening of the primers on the heating element 10, strands are formed that are complementary to the target nucleic acid 22. The denaturing, i.e. the separation of the molecule of the target nucleic acid 22 from the now elongated primers, is not effected due to the overall heating of the entire reaction volume or entire reaction solution, but rather due to a heat pulse caused by a current pulse through the heating elements. The following run of the PCR copying cycle can proceed in a similar manner: the molecules of the original target nucleic acid 22 re-hybridize to primers bound to one or more heating elements, and the polymerase elongates the primers on the heating elements 10, thereby generating complementary strands to the target nucleic acid 22 (or at least to a portion of the target nucleic acid 22). In parallel, other primers, for example forward primers (either suspended freely or also bound to heating elements), can now bind to the elongated parts of the elongated forward primers bound to the heating elements and produced in the first run of the PCR copying cycle (which now represent strands that are complementary to at least a part of the target nucleic acid 22) and the backward primers are then elongated accordingly by the polymerase. As a result, for the first time true copies of at least a part of the original target nucleic acid 22 are produced. The denaturing, i.e. the separation of the double strands generated by means of the elongation by the polymerase (which are in any case bound to the heating apparatus 10 again), is now effected again by means of a heat pulse caused by a current pulse through the heating elements 10. From the third run of the PCR copying cycle onwards, both the original target nucleic acid 22 and the nucleic acid strands generated by the polymerase elongating the primer sequences (which strands are either freely suspended in the reaction volume or bound to the heating elements, depending on the embodiment) now serve as a template for further copying. They are amplified by being hybridized to corresponding primers (either in free suspension or bound to a heating element, depending on the embodiment), followed by elongation by the polymerase and subsequent denaturing by means of a local heat pulse caused by a current pulse through the heating elements 10. The run of the PCR copying cycle just described is preferably repeated many times so as to generate further copies of at least parts of the target nucleic acid 22 in each additional run. For example, the runs are repeated as often as necessary until sufficient numbers of copies of at least parts of the target nucleic acid 22 are present in order to be able detect that the target nucleic acid 22 has been copied or was originally present in the sample. With one of the methods described further above, for example fluorescence methods that make use, for example, of TaqMan chemistry, a molecular beacon and/or intercalating dyes, e.g. SybrGreen, the amplicons thus generated can preferably be detected.

Figure 2B:
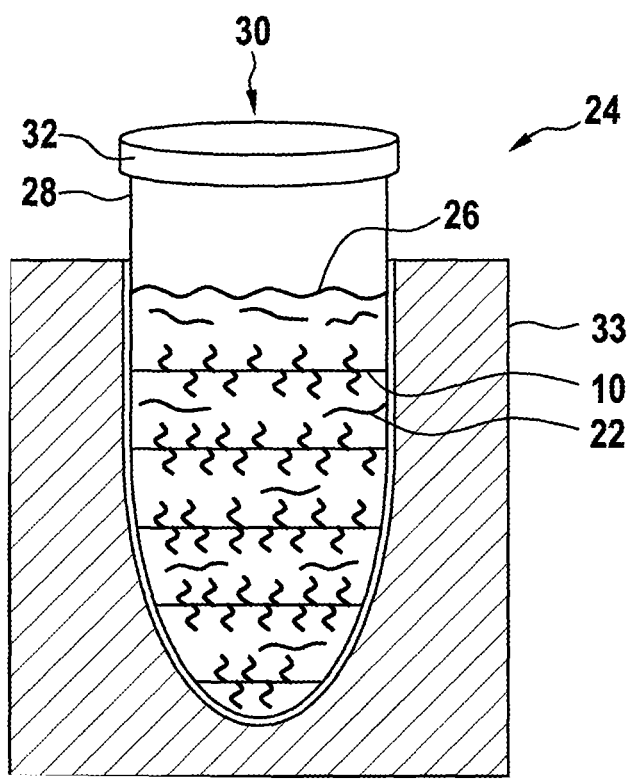

FIG. 2B is a schematic representation of a device 24 for extracting a nucleic acid 22 from a sample liquid 26 according to another preferred embodiment. This embodiment largely corresponds to the embodiment shown in FIG. 2A but, unlike the latter, it additionally comprises an external heating device 33. The heating device 33 is in the form of a heating block in which the reaction vessel 28 can be arranged so as to establish thermal contact between the reaction vessel 28 and the heating device 33. By means of the heating device 33, the reaction solution 26 can then be brought to a base temperature and/or held at the base temperature, for example.

The heating device 33 can thus in particular serve the overall control of the temperature of the reaction solution 26 in the reaction vessel 28; this may be advantageous during the extraction of the nucleic acid 22 and/or during a subsequent amplification or PCR, for example in order to achieve efficient hybridization.

Figure 3A:
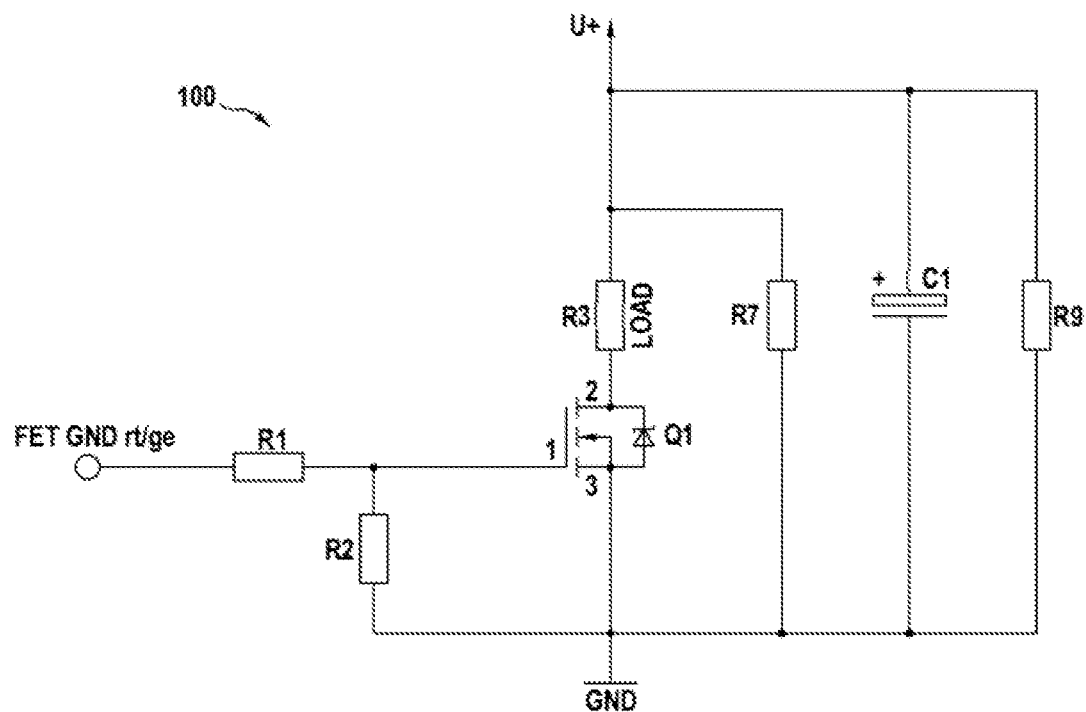
FIG. 3A shows an example of a suitable electrical circuit as a control apparatus and/or power supply for generating electrical pulses for the heating element.

FIG. 3A shows an example of a suitable electrical circuit 100 as a control apparatus and/or power supply 11 for generating electrical pulses in order to apply electrical current to the heating element(s) 10. The circuit is constructed such that a voltage (in this specification always referred to as "U") intended for heating the heating apparatus is applied between earth (GND) and U+ (e.g. a voltage of between 5 and 50 V). The heating apparatus is arranged at the site R3 "Load", and so R3 is the heating apparatus resistor. In the enabled state, the power MOSFET Q1 (IRFP4468, International Rectifier) used by way of example establishes a low-resistance connection between the contact T2 and the contact T3 such that a current flows through the heating apparatus R3. Between earth and the gate (contact T1) of the MOSFET, a control voltage, provided for example by a pulse or frequency generator or an ND converter, is applied via the gate terminal FET GND rt/ge. Pulses measuring 5 V and having a duration of for example between 50 and 500 µs, which allow the MOSFET to be properly connected, are particularly suitable. A capacitor having sufficient capacitance, e.g. >4 mF, and as low an ESR value as possible is provided at site Cl, which makes it possible to maintain the applied voltage for the duration of the heat pulse, even when using low-resistance heating elements 10 (where the resistance of all the heating elements together is typically less than 0.5Ω (ohm)). For example, the resistors R1, R2, R7 and R9 have resistance values of 1, 100 and 24 kΩ (kiloohm).

Figure 3B:
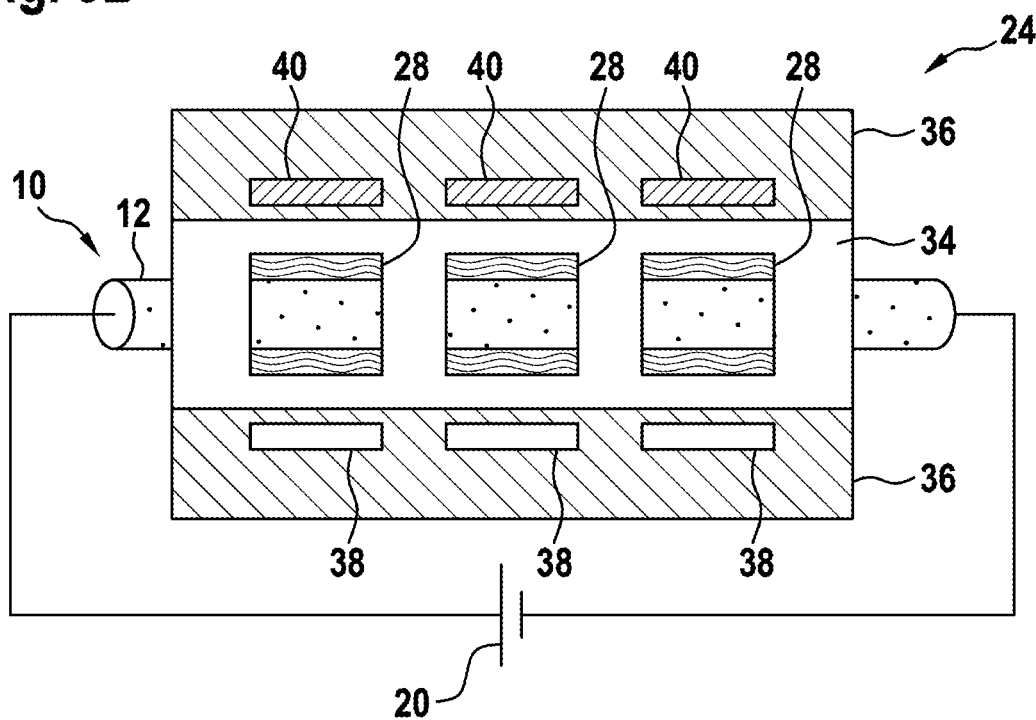
FIGS. 3B and 3C are schematic, simplified cross sections through preferred embodiments of a device for extracting a nucleic acid.

FIG. 3B is a schematic, simplified cross section through an embodiment of a device 24 for extracting a nucleic acid 22, comprising a plurality of reaction vessels 28 and in which the heating elements 10 are formed by portions of a wire 12 that passes through the plurality of reaction vessels 28 and is connected to a voltage source 20. The wire is functionalized by oligonucleotides, which serve both as extraction nucleic acids 14 and primers for an amplification reaction. To simplify the representation, the device for generating electrical pulses is not shown, nor was the drawing made to scale. The wire 12 passes through a plurality of separate reaction vessels 28 in the form of sample liquid chambers (also referred to as wells) in a sample plate 34, which is located between a two-part temperature-control block 36 which serves as an external heating device. The temperature-control block 36 has the function of bringing the reaction volumes in the reaction vessels 28 to the hybridization/elongation temperature and holding them at said temperature. For example, the temperature-control block 36 can be formed as a heating block and/or as a cooling block. To bring the heating elements 10 into contact with the sample liquid and/or with the reaction solution, and/or to separate them therefrom, the sample liquid 26 or reaction solution can be filled into the reaction vessels 28 or suctioned out therefrom, respectively.

In the embodiment shown here, in the lower part of the temperature-control block 36 below each reaction vessel 28 there is an excitation-light source (in this case in the form of an LED 38 having an optical low-pass filter) for exciting a dye in the respective reaction volume, and in the upper part of the temperature-control block 14 above each sample liquid chamber there is a photodiode 40 in the form of a light sensor for detecting the fluorescence of the excited dye in the reaction volumes (said sensor comprising an optical high-pass filter that lets the fluorescent light through). These can be used, for example, to detect the amplified nucleic acid 22 by using suitable dyes, such as intercalating dyes and/or TaqMan probes. The signals from the light sensors can be read out e.g. by an ND converter, and so the time curve of the fluorescence signal can be observed. In particular, the fluorescent light can be recorded, preferably in real-time while carrying out the PCR, as a function of the PCR cycles to thus enable "real-time PCR".

Figure 3C:
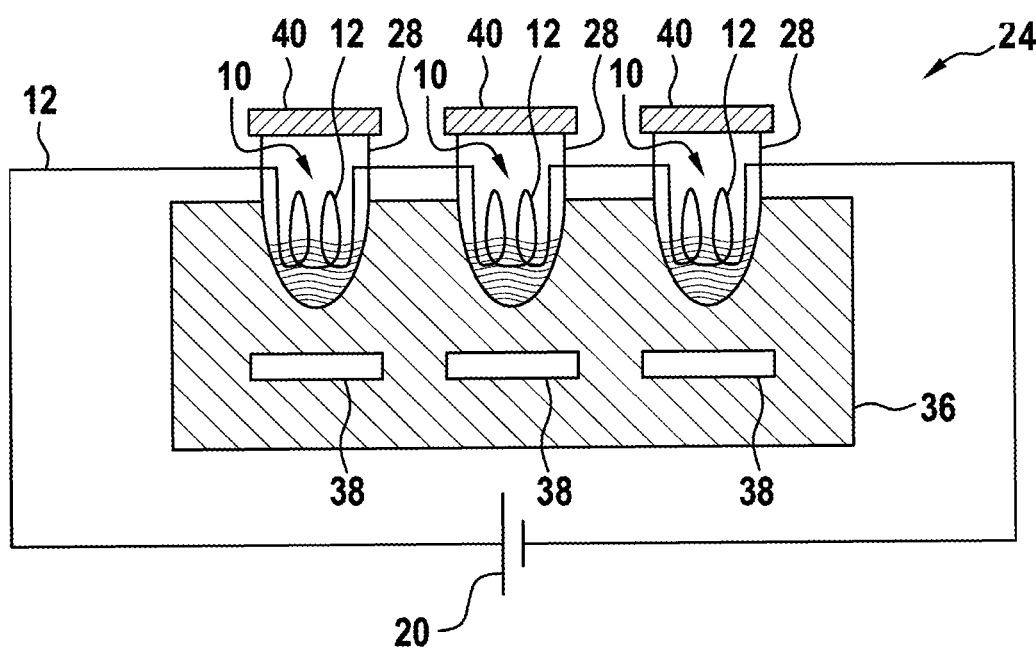

FIG. 3C is a schematic, simplified cross section through a device 24 for extracting a nucleic acid 22 according to another preferred embodiment, which differs from the embodiment of FIG. 3B in that the heating elements 10 are designed as coils from portions of a wire 12 connected to a voltage source 20. To simplify the representation, the pulse generation device is not shown here either. The heating elements 10 in the form of a wire 12 wound into coils are in contact with the reaction volume in the respective reaction vessel 28. Unlike as shown in the figure, they are preferably completely surrounded by the reaction solution. In this embodiment, the reaction vessels 28 are formed as a plurality of separate sample liquid chambers in the form of reaction tubes, which are located in a temperature-control block 36 in order to bring the reaction volumes to the hybridization/elongation temperature and hold them at said temperature. In the embodiment shown here, in the lower part of the temperature-control block 36 below every sample liquid chamber there is an LED 38 acting as an excitation-light source for exciting a dye in the reaction volume, and above each sample liquid chamber there is a photodiode 40 acting as a light sensor for detecting the fluorescence of the excited dye in the reaction volume.

Figure 3D:
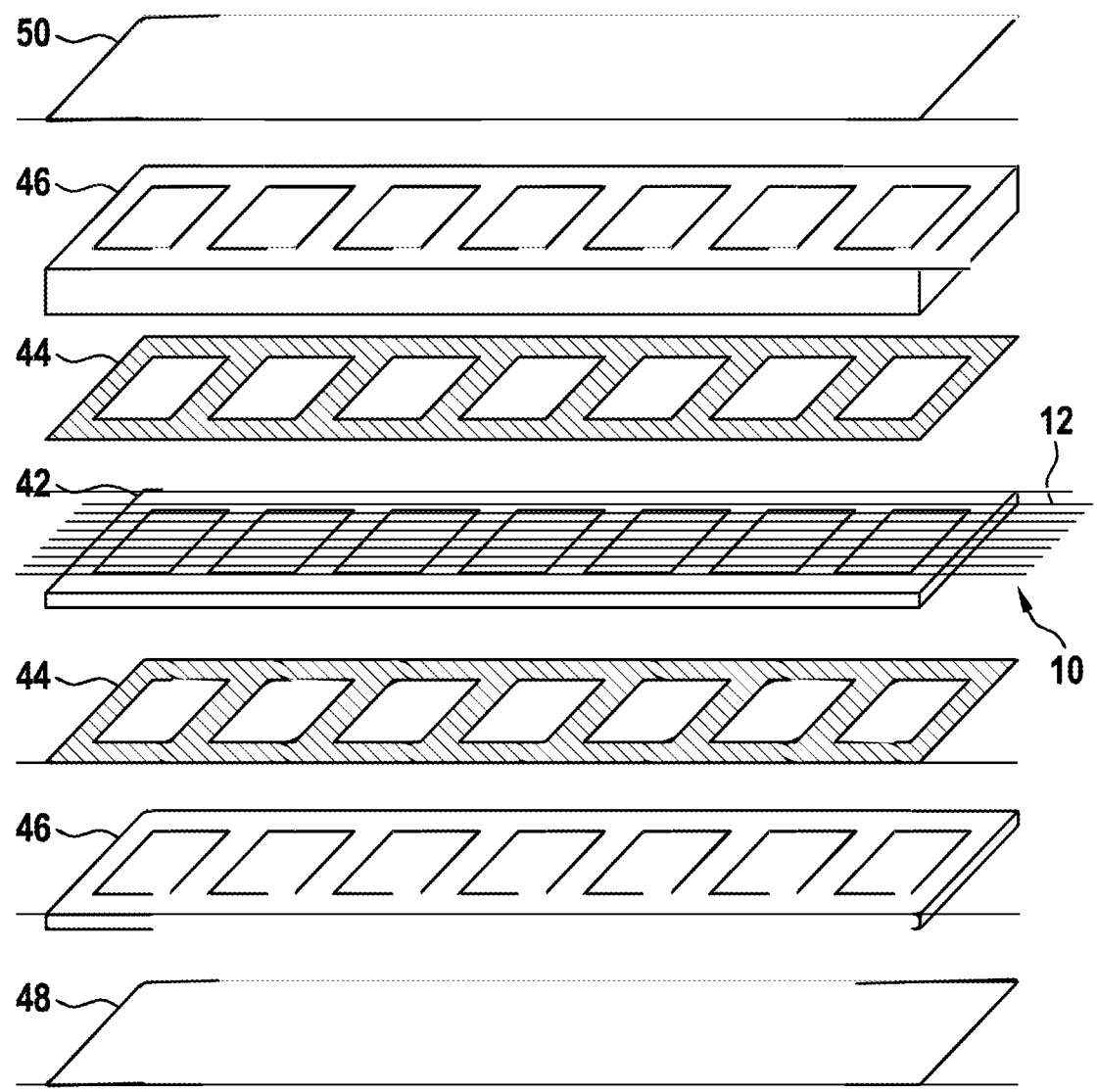
FIG. 3D is a schematic exploded view of a structure of a device for extracting a nucleic acid according to a preferred embodiment.

FIG. 3D schematically shows components from which a sample plate of a device for extracting a nucleic acid 22 according to a preferred embodiment with wire heating elements 10 can be produced. Here, portions of a gold-plated wrapped wire 12 having a diameter of 25 µm (24.8 µm wolfram core with an approximately 100 nm gold sheath, LUMA-METALL AB, Kalmar, Sweden) serve as heating elements 10. Said wire is wound around an acrylic glass plate 42 having a thickness of 0.5 mm (middle plate shown without shading). In the acrylic glass plate 42, there are seven openings (6 mm×6 mm), by which the reaction vessels 28 or sample liquid chambers (wells) are formed. Winding of the wire 12 produces two parallel layers, each consisting of 25 parallel heating elements 10 (a different number of heating elements of typically between 10 and 75 heating elements may also be advantageous depending on the position), in each reaction vessel 28 (only discernible when the device is assembled). Due to the plate, the two layers of heating elements 10 are spaced apart from one another by 0.7 mm; the heating elements 10 within a layer are spaced apart from one another by approximately 0.24 mm. By means, for example, of double-sided adhesive foils 44 (shown with shading, 100-250 µm-thick WEB adhesive tape from 3M) having corresponding recesses for the sample liquid chambers, an additional acrylic glass plate 46 having identical openings is stuck to each side of the wrapped plate 42 (thickness of the lower plate 0.5 mm and thickness of the upper plate 3 mm) and pressed according to the specifications of the manufacturer of the adhesive tape 44. From below, the wells or reaction vessels are sealed, e.g. with a thin foil 48 (shown without shading, Adhesive PCR Foil Seal, 4titude) stuck to the lower acrylic glass plate 46. This produces a sample plate having seven wells through which parallel wires 12 acting as heating elements 10 pass. The wires 12 are interconnected (i.e. all the wires/heating elements are connected in parallel) and electrically contacted at the two outer ends of the sample plate. This makes it possible to send current pulses through all the wells or reaction vessels 28 in a serial manner. The openings in the sample plate (at the top here) can then be sealed with a thin film 50 (shown without shading). According to this preferred embodiment, the sample plates have a width of 20 mm and a length of 90 mm (so that the voltage of the heat pulses drops substantially over a length of approximately 96 mm when the 3 mm excess length of the wires 12 at the ends of the sample plate, as required for contacting, is taken into account). Typically, a total electrical resistance of around 250 milliohms results over the length of the sample plate (with 50 wires connected in parallel).

Figure 4A:
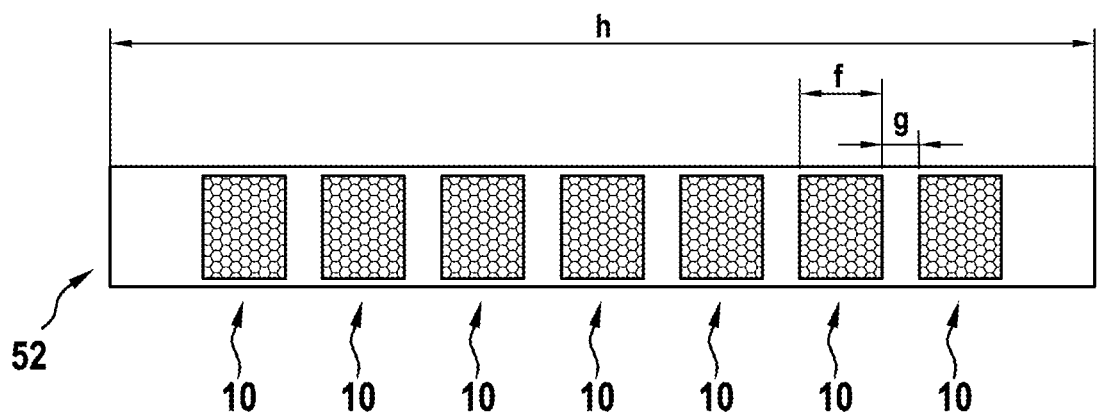
FIGS. 4A and 4B are schematic views of a heating element having a honeycomb structure.
Figure 4B:
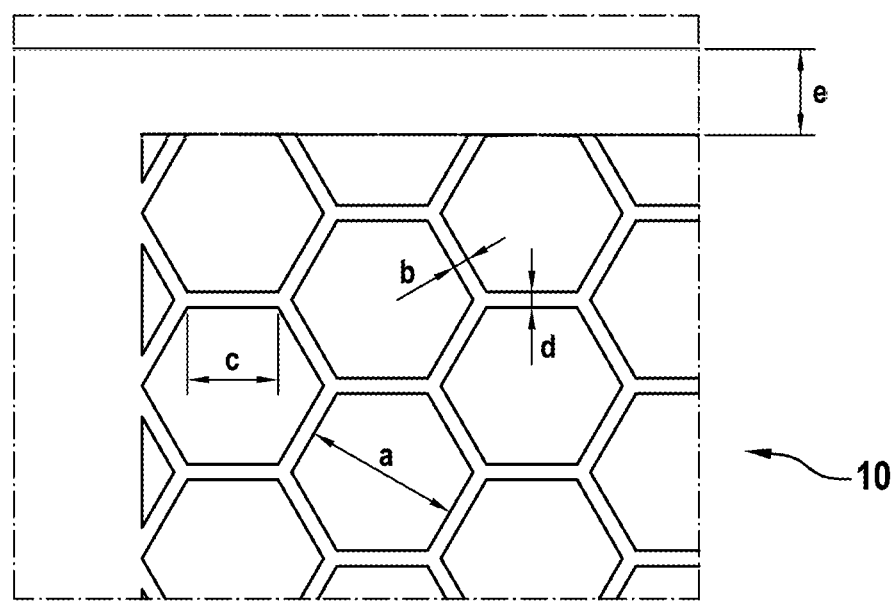

FIGS. 4A and 4B are schematic representations of a preferred embodiment of an arrangement of heating elements 10, wherein the heating elements 10 are formed contiguously in one piece and together form a heating apparatus 52. The heating elements 10 or the heating apparatus 52 has a honeycomb structure. To produce this, a honeycomb structure is generated by photochemical fine-etching processes from a stainless steel foil and then coated with gold. In the embodiment, the lattice is hexagonal, but other lattices or patterns are of course also possible. The current flows through the structure lengthwise, wherein, as shown in FIG. 4A, a honeycomb structure has only been etched in the region of the reaction vessels (not shown in this figure), i.e. where the foil forms the honeycomb-like heating elements 10 to be arranged in a reaction vessel 28. The length f of a heating element 10 is, for example, 8.2 mm and the distance g between the heating elements 10 is, for example, 3.8 mm. The sample chambers or reaction vessels 28 are preferably arranged in the centre above the heating elements 10 and preferably have smaller dimensions (for example 6 mm×6 mm) than the heating elements 10 so as to only use the region of the heating elements 10 that is temperature-controlled as uniformly as possible. The total length h of the foil is 100 mm, for example, i.e. the electrical contacting takes place at the short sides such that the voltage drops over a length of approximately 100 mm. The ridges of the honeycomb structure heat up due to the current conducted through them, and they can denature the double-strand nucleic acid bound thereto.

FIG. 4B is an enlarged representation of the honeycomb structure of a heating element 10 from FIG. 4A having an adjoining edge. In the honeycomb structure shown by way of example, the ridge widths are designed such that as uniform a current density and thus volumetric heating density as possible is achieved throughout the honeycomb structure. In the embodiment example, this is achieved by the width d of the longitudinal ridges being exactly double the width b of the transverse ridges. Example dimensions are 0.87 mm for the honeycomb diameter a, 0.065 mm for the width b of the transverse ridges, 0.5 mm for the ridge length c, 0.13 mm for the width of the longitudinal ridges d and 0.57 mm for the width of a long edge e. The long edge e primarily serves for mechanical stability and is exposed to a different current density than the honeycomb structure.

Below, the invention will be explained in more detail with reference to the technical background and examples, without the invention being limited to these examples. Rather, the examples are possible preferred embodiments used to explain the functioning of the invention.

EXAMPLES

Enzymatic Lysis

The following explanations relate to the production of a sample liquid. A Rinder whole blood sample containing 0.4 mM Tris EDTA is mixed with a defined amount of MRSA bacteria and provided as a sample liquid. To lyse the MRSA bacteria, the enzymes lysozyme and lysostaphin are then added to the sample liquid to achieve a final concentration of 0.1 U/μl lysostaphin and 2 ng/μl lysozyme. This cell suspension with added enzymes, which forms the sample liquid, is incubated for 5 min at 37° C. The cell suspension is then mixed with dissolved Proteinase K (amount: 15% of the sample volume). An AL buffer from Qiagen is also added (amount: 51% of the sample volume mixed with Proteinase K). This suspension is incubated for 5 min at 550 rpm and 56° C. in a thermoshaker. Lastly, the lysate is deactivated for 10 min at 99° C., wherein the genomic DNA is also denatured and fragmented.

Pre-Functionalization of the Heating Elements with Extraction Nucleic Acids and Primers For some preferred embodiments, the heating elements present in reaction vessels of a reaction plate, which are in the form of gold-coated wires are incubated beforehand, i.e. before the sample liquid is added, together with a functionalization solution (see Table 2) for at least three hours at room temperature. To be subsequently used to extract nucleic acids, each reaction vessel is first washed five times with deionized water, the water being removed from the reaction chamber following each wash.

Extracting the Nucleic Acid Using Pre-Functionalized Heating Elements

The nucleic acid is extracted from the sample liquid using the heating elements, which have been pre-functionalized with extraction nucleic acids as described above, substantially within the context of a pre-hybridization of the nucleic acids with the extraction nucleic acids bound to the heating elements. The extraction comprises at least one hybridization step and one or more washing steps. The hybridization step is divided into two steps. In the first hybridization step, the sample liquid, which is in the form of an enzymatic lysate, is pipetted into the reaction vessel comprising the functionalized heating elements. Next, the reaction vessel is sealed with a self-adhesive foil and then incubated for 5 min at 45° C., wherein the heating is realized by an external heating device (i.e. not via the wires serving as heating elements, but instead by a heating block located below and above the sample carrier). In the second hybridization step, the reaction vessel filled with the lysate is unsealed after a two-minute rest phase at room temperature. In one washing step, each reaction vessel is washed twice using a special washing solution (see Table 4) and the washing solution is removed again after each wash. Once the nucleic acid has been extracted, the reaction solution required for the PCR to detect the resistance gene MecA occurring in the MRSA genome (see Table 1) is pipetted into each of the reaction vessels, which are then sealed again. According to this example, the temperatures required for the amplification are provided by a device for amplifying a nucleic acid having the settings stated in Table 3, wherein the device has an external heating device 33 that is in the form of a heating block, the block temperature of which can be set to the desired base temperature, for example, in order thereby to control the temperature of the reaction solution 26 to the base temperature. Furthermore, the device has a heatable cover 32, which seals the reaction vessel 28 and the temperature of which can be controlled so as to prevent or reduce condensation of the vaporous proportion of the reaction solution 26 on the cover 32. For this purpose, the temperature of the cover 32 is particularly preferably brought to a temperature that is a few degrees Celsius above the base temperature. The cover 32 can, for example, also be in the form of a heating block and be designed to be able to simultaneously cover a plurality of reaction vessels 28.

Nucleic Acid Copying

All the sequences named below are listed in the appendix at the end of the description.

Table 1: List of the Constituents for the Reaction Solution for Carrying Out the Amplification Reaction:

TABLE 1

List of the constituents for the reaction solution for carrying out the amplification reaction:

| Substance | Concentration |
| --- | --- |
| H$_2$O | — |
| Tris pH 9 | 20 mM |
| MgCl$_2$ | 3 mM |
| Apta Taq Genotyping Master (Roche) | 1x |
| Reverse primer containing sequence 1 (see appendix): | 500 nM |

TABLE 1-continued

List of the constituents for the reaction solution
for carrying out the amplification reaction:

| Substance | Concentration |
|---|---|
| TaqMan probe containing sequence 5'FAM-[sequence 2]-3'BHQ1 | 50 nM |
| Uracil-DNA glycosylase UDG (PEQLAB) | 2.4 U/µl |

TABLE 2

Constituents of the functionalization solution:

| Substance | Concentration |
|---|---|
| Phosphate buffer pH 7 | 5 mM |
| NaCl | 10 mM |
| MgCl$_2$ | 100 mM |
| Thiol-modified forward primer containing sequence 5'Thiol - [sequence 3]/iSp9/[sequence 4] | 100 mM |

The designation/iSP9/indicates an abasic modification "spacer 9", which serves to prevent the multi-A spacer sequence (sequence 3) being overwritten or complemented by the polymerase. The spacer is an internal spacer, i.e. the spacer is not incorporated at an end of the oligonucleotides, but rather is integrated internally in the nucleotide chain. The spacer sequence which is arranged between the 5'-thiol binding site and the extraction sequence (sequence 4) can provide the advantage that said extraction sequence is more easily accessible in spatial terms due to its greater distance from the heating element. For the amplification reaction, the reaction solution is preferably provided with a volume of at least 10 µl and at most 100 µl.

TABLE 3

Physical parameters for carrying out a subsequent PCR
amplification reaction by locally heating the heating
elements of the device or in the sample carrier:

| Parameter | Value |
|---|---|
| Voltage | ~38 V |
| Total heating resistance of the heating elements (49 wires of 25 µm diameter) | ~250 mΩ |
| Pulse duration | 150 µs |
| Cycle duration | 1.5 s |
| Block temperature = base temperature (external heating block below the sample carrier) | 66° C. |
| Cover temperature (external heating block in the form of a heatable cover resting on the sample carrier or reaction vessels to prevent condensation) | 73° C. |
| Duration of pre-heating up to base temperature (ensured by external heating blocks of the external heating device) | 120 s |

When using the selected physical parameters, energy of for example W≈150 µs·(38V)$^2$/250 mΩ≈0.9 J is input per denaturing step in each PCR cycle. This energy is distributed across both the entire sample plate and the PCR reaction solution, which has a volume of approximately 0.5 ml in the entire sample plate (e.g. when approximately 62 µl PCR volume is used in each of eight chambers). Even if it is assumed that the heat capacity of the sample plate and of the heating elements is completely negligible, and the total energy is input only into the reaction solution, the overall temperature increase in the reaction solution is at most $$\Delta T = \frac{w}{m \cdot c} = \frac{0.9 J}{0.5 \text{ ml} \cdot 1 \frac{g}{ml} \cdot 4.2 \frac{J}{g \cdot °C.}} = 0.43° \text{ C.},$$

wherein, for the heat capacity c of the reaction solution, the value for water (c=4.2 J/(g° C.)) has been assumed here.

By contrast, in order to achieve a minimum 20° C. temperature increase in a PCR solution of this kind during the denaturing step in a conventional PCR, energy of $$W = m \cdot c \cdot \Delta T = 0.5 \text{ ml} \cdot 1 \frac{g}{ml} \cdot 4.2 \frac{J}{g \cdot °C.} \cdot 20° \text{ C.} = 42$$

J would thus need to be input as a minimum.

Throughout the duration of the PCR, the fluorescence of a TaqMan probe using an FAM dye as an emitter is recorded for each of the sample chambers. For this purpose, each sample chamber is illuminated with excitation light during the PCR and the emission light is recorded in order to record real-time data in this way.

TABLE 4

Constituents of the washing solution for cleaning the
heating elements to remove sample-liquid residues:

| Substance | Concentration |
|---|---|
| H$_2$O | — |
| MgCl$_2$ | 9 mM |
| Tris pH 8 | 10 mM |

Amplification of the Nucleic Acids without Prior Extraction

As a reference test, a PCR reaction was carried out using the same device but without any prior extraction. The heating elements were functionalized with primers for the PCR but the heating elements were not brought into contact with a sample liquid prior to the amplification. Instead, right at the start the heating elements were brought into contact with a reaction solution for the PCR, into which a predetermined (low) amount of sample liquid containing the target nucleic acid as the target was then introduced into the reaction solution. In particular, the amount of sample liquid introduced into the reaction solution is so low that it does not hinder and/or prevent the PCR from being carried out in the reaction solution. Different amounts of the blood lysate or sample liquid were added directly to the reaction solution for different measurements. In the case of a blood lysate containing 100 colony forming units (CFUs) of MRSA bacteria per microlitre (CFU/µl) (the DNA of which was released during the enzymatic lysis), a positive TaqMan fluorescence signal could be detected after approximately 8 min when the blood lysate was mixed into the reaction solution directly and only accounted for 1% of the final PCR reaction volume (0.6 µl blood lysate with a total PCR volume of 60 µl). If, however, the added amount of blood lysate is increased to 3% of the final PCR reaction volume, it is no longer possible to detect a positive TaqMan fluorescence signal. In this case, more DNA copies would also be introduced into the reaction solution due to the greater amount of sample used. However, these would no longer be able to be amplified or detected since excessive amounts of disruptive constituents or substances would have entered the PCR reaction or reaction solution from the blood lysate and the reaction solution would contain too many impurities.

Figure 5:
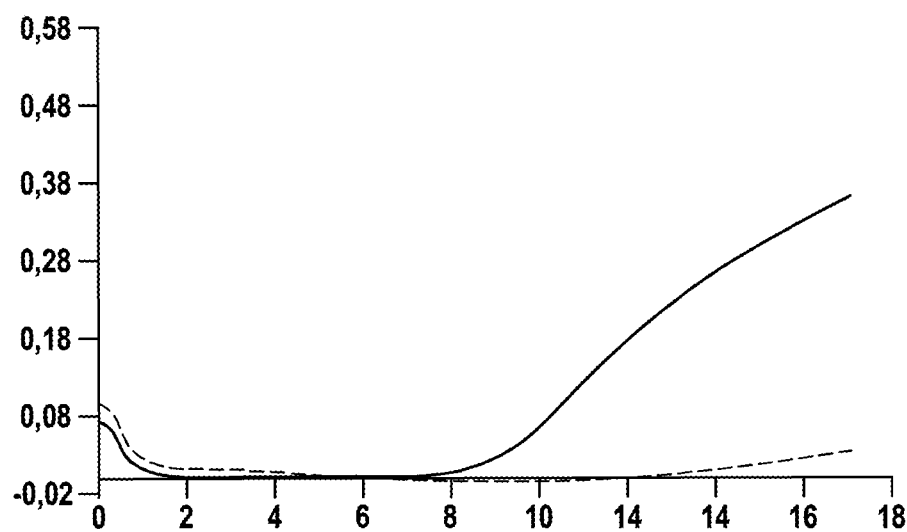
FIGS. 5 to 8 are graphs showing fluorescence signals that have been measured with PCR amplification reactions on the basis of various sample liquids.

The results of these measurements are shown in the graphs in FIG. 5, in which the time in minutes is plotted on the horizontal axis and the measured fluorescence signal is plotted in arbitrary units on the vertical axis. The graphs shown represent the amplification curves of the PCR reactions, wherein the solid line represents the measurement at which 1% blood lysate was mixed into the reaction solution, and the dashed line represents the measurement at which 3% blood lysate was mixed into the reaction solution. In each case, the blood lysate contained 100 CFU/µl. When comparing the two amplification curves, it can be clearly seen that the PCR reaction with 3% blood lysate in the reaction solution did not achieve any positive amplification result, even though the number or concentration of the CFUs or of the nucleic acids released therefrom is three times as great as in the case of the other amplification curve. However, the amplification curve for the measurement with 1% blood lysate in the reaction solution (solid line) shows a sharp increase in the amplification signal after approximately 8 min, thus indicating a positive amplification result. This demonstrates that the sensitivity of the amplification reaction cannot be improved by simply increasing the concentration of a blood lysate mixed into the reaction solution or a sample liquid mixed into the reaction solution, since in this case the substances contained in the sample liquid or blood lysate disrupt the amplification reaction and/or prevent detection.

Figure 6:
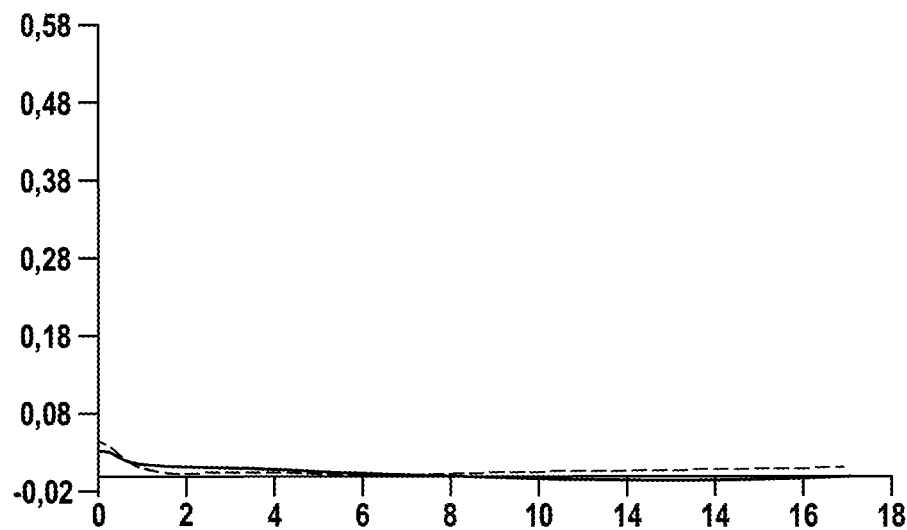

If the originally added amount of bacteria or CFUs in the blood lysate is reduced such that the blood lysate contains only 1 CFU/µl, the nucleic acids cannot be positively detected in the PCR reaction either at 1% or at 3% blood lysate content. In the case of a 1% sample content, admittedly, no pronounced inhibition or hindrance of the amplification reaction is anticipated in view of the results shown in FIG. 5. In statistical terms, however, only nucleic acids from six CFUs still enter the amplification reaction, which, under the present circumstances, may no longer be reliably detectable. The results of this comparative measurement are shown in FIG. 6, in which the duration in minutes is likewise plotted on the horizontal axis and the fluorescence signal is plotted in arbitrary units on the vertical axis. Neither of the amplification reactions, in which the blood lysate had a bacteria concentration of only 1 CFU/µl before being mixed in, supplies any detectable amplification signal, either with a content of 1% (solid line) or 3% blood lysate mixed into the reaction solution.

Extraction and Subsequent Amplification of the Nucleic Acids

In further experiments, in each case 80 µl blood lysate as the sample liquid having a bacteria concentration of 100 CFU/µl or 1 CFU/µl were treated using an extraction method according to a preferred embodiment in order to at least partly extract, prior to amplification, the nucleic acids to be amplified. For this purpose, after having been pre-functionalized with extraction nucleic acids, which also serve as forward primers in the amplification, the wires used as heating elements in the reaction chambers were brought into contact with the blood lysate, i.e. with the sample liquid, by filling the respective sample liquid into the reaction vessels. The nucleic acid from the sample liquid could then hybridize with the extraction nucleic acids, which had been pre-functionalized to the wires, bound to the heating elements in the form of oligonucleotides. For this purpose, the temperature of the entire sample carrier, and thus also the sample solution and heating elements in the sample chambers or reaction vessels, was controlled to 45° C. for 5 min by an external heating block below the sample carrier, in order to enable hybridization at said temperature, followed by a two-minute rest phase at room temperature. The removal of the sample liquid and the subsequent washing steps removed the constituents or substances detrimental to the amplification reaction from the sample liquid and left behind the extracted nucleic acids hybridized to the wire. Next, each reaction vessel was filled with 60 µl reaction solution, provided as a PCR mastermix according to Table 1, and the PCR was carried out using local heating by means of the heating elements.

Figure 7:
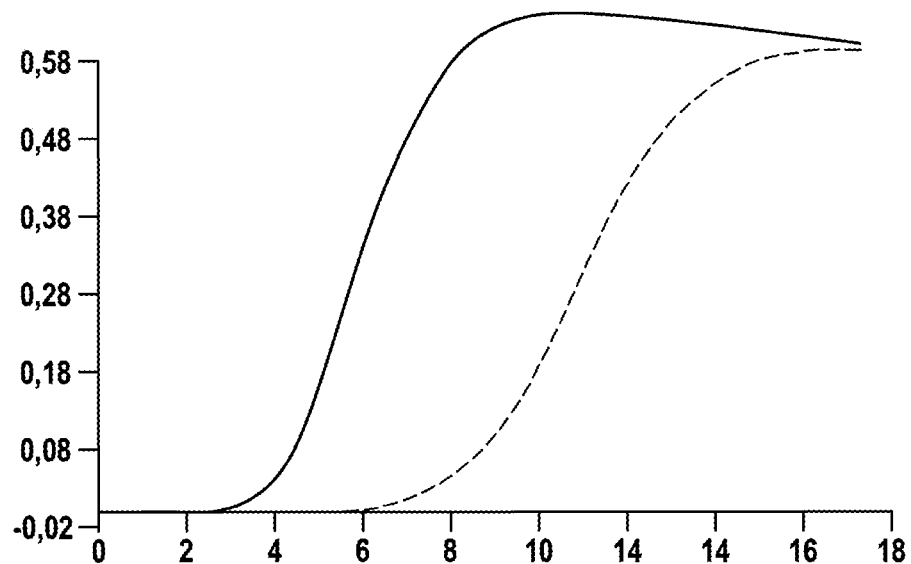

The results of these PCR reactions are shown in a graph in FIG. 7, in which once again the duration in minutes is plotted on the horizontal axis and the fluorescence signal is plotted on the vertical axis. The PCR in which the sample liquid had a bacteria concentration of 100 CFU/µl (solid line) now already shows a positive amplification result or fluorescence signal after only approximately 3 minutes, and even the PCR in which the sample liquid had a bacteria concentration of only 1 CFU/µl (dashed line) supplied a clear fluorescence signal, which increased after around 8 min, and a clear amplification result. By contrast, if a blood lysate that had not had MRSA bacteria added beforehand was used, the corresponding measurement remained negative (data not shown here) and therefore did not supply a positive amplification result. This therefore illustrates that, by using a method according to the invention, the extraction of nucleic acids from a sample liquid that contains substances detrimental to the amplification and therefore cannot be directly added to the reaction solution with a high concentration, the sensitivity of amplification reactions can be considerably improved. The lysate is not limited to a particular starting substance or lysate type. For example, the lysate can be present in the form of blood lysate. The blood lysate can have been lysed in different ways, such as chemically and/or mechanically, e.g. by means of ultrasonic action, which means that the method can be applied flexibly to many different lysate starting forms. Comparable results could also be obtained correspondingly with plasma, serum and nasal swab lysates. The method according to the invention is therefore suitable for a wide range of different sample liquids.

Extracting the Nucleic Acids Using Heating Elements that have not been Pre-Functionalized For comparison with the above-described method, a method was now used in which, unlike the above-described method, wires that had not been pre-functionalized were used as heating elements in the reaction vessels, i.e. in which the heating elements had not been pre-functionalized with extraction nucleic acids. By contrast, before being brought into contact with the wires, the blood lysate or sample liquid was mixed with extraction nucleic acids that were in the form of oligonucleotides and had a thiol group with which they could bind to a gold surface (final concentration 100 mM), and was placed into the reaction vessel containing the non-functionalized gold wires together with the other constituents of the sample liquid. The reaction vessel was then sealed and incubated for 10 min at 45° C. Following a two-minute rest phase at room temperature, the reaction vessel was unsealed again. Next followed washing processes and the carrying out of a PCR, in each case precisely as described above.

As the inventors noted, a positive amplification signal could also be detected in this case. This is surprising since, when excess extraction nucleic acids free in solution are used, hybridization between extraction nucleic acids not bound to wires and target nucleic acids appears preferable, since according to this embodiment both the excess extraction nucleic acids not bound to wires and the target nucleic acids are distributed homogeneously within the solution. According to expectations, the extraction nucleic acids that bind to the heating elements as the heating elements are brought into contact with the sample liquid should be outnumbered, and since they are immobilized, they should be more difficult to access for the freely suspended nucleic acid to be extracted than for the excess extraction nucleic acids that are free in the sample liquid and not bound to wires, i.e. not bound to a heating element. Accordingly, a person skilled in the art would expect few target nucleic acids bound to the wires, and thus significantly poorer or non-existent extraction and amplification. Additionally, contrary to expectations, the inventors discovered that, under the chemical conditions in the blood lysate or sample liquid, the wires are functionalized with functionalization oligomers, e.g. with the extraction nucleic acid, since the functionalization typically has to be effected under considerably different chemical conditions (see Table 2).

However, this embodiment makes it possible, in a surprisingly reliable manner, to successfully extract and amplify the nucleic acids using wires that have not been pre-functionalized, i.e. heating elements, that have not been functionalized beforehand with extraction nucleic acids. The fact that the extraction nucleic acids cannot become attached to the heating elements and functionalise said elements until the heating elements are being brought into contact with the sample liquid does not hinder the functioning of the method according to the invention in accordance with this embodiment. Not only can the method for extracting the nucleic acid be simplified thereby, but the production and/or storage and/or shipping of the device and/or the necessary components can also be simplified, and/or the ability to customize devices for extracting nucleic acids or heating elements according to customer-specific requirements can be improved.

Figure 8:
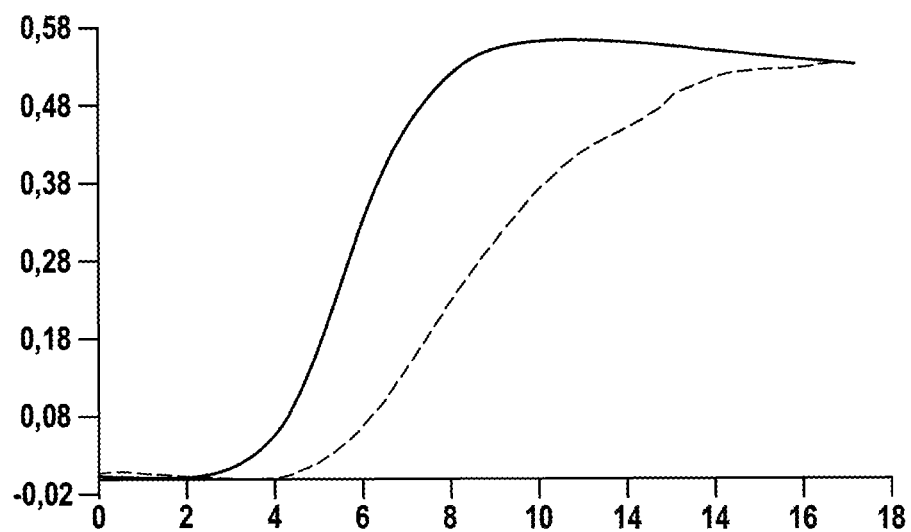

The results of the experiments just described are shown in the graph in FIG. 8, in which once again the duration in minutes is plotted on the horizontal axis and the fluorescence signal is plotted on the vertical axis. Both graphs were obtained using a blood lysate containing 100 CFU/µl. The solid amplification curve corresponds to the amplification using pre-functionalized gold wires as heating elements. The dashed amplification curve corresponds to the amplification using gold wires that had not been pre-functionalized as heating elements.

LIST OF REFERENCE NUMERALS 10 heating element
12 wire or heating wire
4 extraction nucleic acid
15 adapter nucleic acid
16 power supply
8 switch
20 voltage source
22 nucleic acid (to be extracted)
24 device for extracting a nucleic acid
26 sample liquid
28 reaction vessel
30 opening (in the reaction vessel)
32 cover
34 sample plate
36 temperature control block
38 LED
40 photodiode
42 acrylic glass plate
44 adhesive tape
46 acrylic glass plate
48 foil
50 foil
52 heating apparatus
100 electrical circuit for power supply

APPENDIX

Sequence list
(sequence from 5' to 3' in each case):

Sequence 1: TGAAGATGTGCTTACAAGTGCTA
(SEQ ID No. 1)

Sequence 2: TCCACCCTCAAACAGGTGAATTAT
(SEQ ID No. 2)

Sequence 3: AAAAAAAAAAAAAAAAAAAAAAAAAAAAAAAAAAA
(SEQ ID No. 3)

Sequence 4: AAATGATTATGGCTCAGGTACTGC
(SEQ ID No. 4)

What is claimed is:

1. A device comprising:
a reaction vessel to contain a liquid including at least one of a sample liquid and a reaction solution; and
a heating element connected to and disposed in the reaction vessel, the heating element being connected to an adapter nucleic acid structured to bind to an extraction nucleic acid, wherein the extraction nucleic acid is at least partly complementary to a nucleic acid from the sample liquid, and wherein the heating element is heatable to a temperature that is equal to or higher than a denaturing temperature of the adapter nucleic acid bound to the extraction nucleic acid.

2. The device of claim 1, wherein the heating element comprises the extraction nucleic acid bound to the adapter nucleic acid such that the extraction nucleic acid is indirectly bound to the heating element.

3. The device of claim 1, wherein the heating element is formed as part of the reaction vessel and is disposed in the reaction vessel such that the liquid is to cover the heating element, and wherein the reaction vessel comprises at least one opening for at least one of (i) adding the sample liquid to the reaction vessel or (ii) removing the reaction solution from the reaction vessel.

4. The device of claim 3, wherein the heating element is a wire with an electrically conductive body which has an extent R, perpendicular to a direction of current flow, in every spatial direction perpendicular to the direction of current flow, the extent R being at least 0.2 µm and at most 0.5 mm.

5. The device of claim 1, wherein the device has multiple heating elements, each of the multiple heating elements including a wire disposed within the reaction vessel.

6. The device of claim 1, wherein the device is configured to carry out an amplification reaction to copy the nucleic acid from the sample liquid, wherein the heating of the heating element is effected such that only an area immediately surrounding the heating element is locally heated at least to the denaturing temperature.

7. The device of claim 1, further comprising at least one primer for a polymerase chain reaction for copying the nucleic acid from the sample liquid, the primer being bound to the heating element.

8. The device of claim 1, wherein the extraction nucleic acid is adapted for a polymerase chain reaction for copying the nucleic acid from the sample liquid.

9. The device of claim 1, wherein the heating element is configured to be brought in contact with the sample liquid, such that the sample liquid surrounds the heating element, and to connect to the extraction nucleic acid when the extraction nucleic acid is provided in the sample liquid.

10. The device of claim 1, wherein the device is configured such that the heating element is heatable in a manner that only the heating element and an area immediately surrounding the heating element are heated to the denaturing temperature or to a higher temperature at which the adapter nucleic acid bound to the extraction nucleic acid at least partly melts or denatures.

11. The device of claim 1, wherein the device is configured such that the heating element is heatable by at least one heating process, which is effected such that the heating of the heating element per heating process and across all the heating processes increases an average temperature of a reaction solution by no more than 5° C.

12. The device of claim 1, wherein the adapter nucleic acid is bound directly to a surface of the heating element via a thiol bond.

13. The device of claim 1, further including an electrical circuit to apply electrical pulses to the heating element to effect the heating, in a heating zone of the liquid, extending no more than 100 micrometers from the heating element, and to effect cooling in the heating zone by distribution of input energy supplied by the heating element to the remainder of the liquid in the reaction vessel.

14. An apparatus comprising:
a reaction vessel to contain a liquid including at least one of a sample liquid and a reaction liquid;
a heating element connected to and disposed in the reaction vessel such that the liquid is to cover the heating element;
an adapter nucleic acid connected to the heating element, wherein the adapter nucleic acid is structured to bind to an extraction nucleic acid that is at least partly complementary to a nucleic acid from the sample liquid; and
an electrical circuit to heat the heating element to a temperature that is equal to or higher than a denaturing temperature of the adapter nucleic acid bound to the extraction nucleic acid.

15. The apparatus of claim 14, wherein the electrical circuit is to apply electrical voltage or current pulses to the heating element to heat the heating element and, in response, cause the heating element to heat and to input energy to a heating zone of the liquid.

16. The apparatus of claim 15, wherein the electrical circuit is to effect cooling in the heating zone of the liquid by discontinuance of the application of the electrical voltage or current pulses to distribute the input energy supplied by the heating element to the remainder of the liquid in the reaction vessel.

17. The apparatus of claim 14, wherein the heating element includes a wire that is disposed within the reaction vessel such that the sample liquid is to surround the heating element on multiple surfaces of the wire.

18. The apparatus of claim 14, wherein the heating element is anchored to the reaction vessel.

19. The apparatus of claim 14, further including:
- a plurality of reaction vessels, including the reaction vessel, wherein the heating element includes a wire that passes through and in each of the plurality of reaction vessels and is connected to the electrical circuit; and
- a plurality of adapter nucleic acids, including the adapter nucleic acid, connected to the wire.

20. The apparatus of claim 19, wherein the electrical circuit is to apply an electrical pulse to the wire such that the electrical pulse is sent through each of the plurality of reaction vessels in a serial manner, and in response, to heat the heating element.

\* \* \* \* \*